(12) United States Patent
Zheng et al.

(10) Patent No.: US 9,121,859 B2
(45) Date of Patent: Sep. 1, 2015

(54) COMPOUNDS AND METHODS FOR DETERMINATION OF FKBP-BINDING IMMUNOSUPPRESSANT DRUGS

(71) Applicant: Siemens Healthcare Diagnostics Inc., Tarrytown, NY (US)

(72) Inventors: Yi Feng Zheng, Wilmington, DE (US); Tie Q. Wei, Wilmington, DE (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 371 days.

(21) Appl. No.: 13/693,229

(22) Filed: Dec. 4, 2012

(65) Prior Publication Data

US 2014/0154706 A1 Jun. 5, 2014

(51) Int. Cl.
  *G01N 33/53* (2006.01)
  *A61K 31/436* (2006.01)
  *G01N 33/94* (2006.01)

(52) U.S. Cl.
  CPC .......... *G01N 33/9493* (2013.01); *A61K 31/436* (2013.01); *G01N 33/5308* (2013.01)

(58) Field of Classification Search
  CPC ........... G01N 33/9493; G01N 33/5308; A61K 31/436
  See application file for complete search history.

(56) References Cited

U.S. PATENT DOCUMENTS

| | | | |
|---|---|---|---|
| 4,661,408 A | 4/1987 | Lau et al. | |
| 5,023,262 A | 6/1991 | Caufield et al. | |
| 5,128,103 A | 7/1992 | Wang et al. | |
| 5,147,529 A | 9/1992 | Lee et al. | |
| 5,151,348 A | 9/1992 | Lau et al. | |
| 5,158,871 A | 10/1992 | Rossomando et al. | |
| 5,302,532 A | 4/1994 | Lau | |
| 5,422,284 A | 6/1995 | Lau | |
| 5,434,051 A | 7/1995 | Allard et al. | |
| 5,447,870 A | 9/1995 | Lau | |
| 5,798,355 A * | 8/1998 | Steiner et al. | 514/248 |
| 5,843,960 A | 12/1998 | Steiner et al. | |
| 6,328,970 B1 | 12/2001 | Molnar-Kimber | |
| 6,887,669 B1 | 5/2005 | Staples et al. | |
| 7,186,518 B2 | 3/2007 | Wang et al. | |
| 7,476,678 B2 | 1/2009 | Graziani et al. | |
| 7,714,118 B2 | 5/2010 | Reeves et al. | |

(Continued)

FOREIGN PATENT DOCUMENTS

EP 0778023 B1 3/2003

OTHER PUBLICATIONS

Timothy D. Ocain, et al., A Nonimmunosuppressive Triene-Modified Rapamycin Analog Is a Potent Inhibitor of Peptidyl Prolyl Cis-Trans Isomerase, Biochemical and Biophysical Research Communications, May 14, 1993, 1340-1346, vol. 192, No. 3, Academic Press, Inc.

(Continued)

*Primary Examiner* — Shafiqul Haq
(74) *Attorney, Agent, or Firm* — Theodore J. Leitereg

(57) ABSTRACT

Compositions are disclosed for releasing an FKBP-binding immunosuppressant drug from endogenous binding substances in a sample suspected of containing the FKBP-binding immunosuppressant drug. The compositions include sirolimus derivatives that are modified with a bulky organic radical in the triene portion of the sirolimus molecule. The compositions may be employed in conjunction with assays for an FKBP-binding immunosuppressant drug in a sample suspected of containing the drug.

15 Claims, 6 Drawing Sheets

(56) References Cited

U.S. PATENT DOCUMENTS 8,173,442 B2 5/2012 Holmquist et al.
2011/0318754 A1 12/2011 Wei

OTHER PUBLICATIONS

C.E. Caufield, Structure-Activity Relationships Involving Modification to Macrolides FK-506 and Rapamycin, Current Pharmaceutical Design, 1995, 145-160, vol. 1, Benham Science Publishers B.V.

Champion C.S. Deivanayagam et al., "Structure of FKBP12.6 in Complex with Rapamycin", 2000, Acta Crystallographica, vol. D56, pp. 266-271.

Steven J. Soldin, "Role of Immunophilins in Therapeutic Drug Monitoring of Immunosuppressive Drugs", Jul. 1998, Clinical Biochemistry, vol. 31, No. 5, pp. 381-384.

C. E. Caufield, "Structure-Activity Relationships Involving Modifications to the Macrolides FK-506 and Rapamycin", 1995, Current Pharmaceutical Design, vol. I, pp. 145-160.

Alexander A. Grinfeld et al., "Acid Catalyzed Functionalization of Rapamycin", 1994, Tetrahedron Letters, vol. 35, No. 37, pp. 6835-6838.

Frank Jensen et al., "Reaction of 4-Phenyl-1,2,4-triazoline-3,5-dione with Substituted Butadienes. A Nonconcerted Diels-Alder Reaction", 1987, J. Am. Chem. Soc., vol. 109, pp. 6367-6385.

Waldemar Adam et al., "Reaction of 4-Phenyl-1,2,4-triazoline-3,5-dione (PTAD) with Bicyclic Monoterpenes", 1982, Chem. Ber., vol. 115, pp. 1982-1989.

Ursula Biermann et al., "Regio—and Stereoselective Diels-Alder Additions of Maleic Anhydride to Conjugated Triene Fatty Acid Methyl Esters", 2007, Eur. J. Org. Chem, pp. 3859-3862.

Stephen F. Nelsen et al., "Addition of N-Methyltriazolinedione to Biadamantylidene", 1997, Journal of Physical Organic Chemistry, vol. 10, pp. 456-460.

Steven J. Hamrock et al.,"Photochemical Diels-Alder Addition of N-Methyltriazolinedione to Phenanthrene", 1988, Tetrahedron Letters, vol. 29, No. 43, pp. 5509-5512.

D.P. Kjell et al., "A Photochemical Diels-Alder Reaction of N-Methyltriazolinedione", 1985, Journal of Photochemistry, vol. 28, pp. 205-213.

Leo A. Paquette et al., "Electronic Control of Stereoselectivity. 7. Stereospecificity of N-methyltriazolinedione cycloaddition to tricyclo[5.2.1.02,6]deca-2,5-diene, tricyclo[5.2.1.02,6]deca-2,5,8-triene, and tricyclo[5.2.2.02,6] undeca-2,5,8-triene", 1980, J. Org. Chem., vol. 45, pp. 4922-4926.

Timothy D. Ocain et al., "A Nonimmunosuppressive Triene-Modified Rapamycin Analog Is a Potent Inhibitor of Peptidyl Prolyt Cis-Trans Isomerase", May 14, 1993, Biochemical and Biophysical Research Communications, vol. 192, No. 3, pp. 1340-1346.

International Search Report and Written Opinion of International Application No. PCT/US2013/072716 dated Apr. 4, 2014.

* cited by examiner

Sirolimus

Tacrolimus

COMPOUNDS AND METHODS FOR DETERMINATION OF FKBP-BINDING IMMUNOSUPPRESSANT DRUGS

BACKGROUND

The invention relates to compounds, methods and kits for the determination of FKBP-binding immunosuppressant drugs, such as sirolimus compounds and tacrolimus compounds, in samples, such as patient samples, known or suspected to contain such FKBP-binding immunosuppressant drugs.

The body relies upon a complex immune response system to distinguish self from non-self. At times, the body's immune system must be controlled in order to either augment a deficient response or suppress an excessive response. For example, when organs such as kidney, heart, heart-lung, bone marrow and liver are transplanted in humans, the body will often reject the transplanted tissue by a process referred to as allograft rejection.

In treating allograft rejection, the immune system is frequently suppressed in a controlled manner with drug therapy. Immunosuppressant drugs are carefully administered to transplant recipients in order to help prevent allograft rejection of non-self tissue. Two most commonly administered immunosuppressive drugs to prevent organ rejection in transplant patients are Cyclosporine (CSA) and FK-506 (FK or tacrolimus). Another drug that finds use as an immunosuppressant in the United States and other countries is sirolimus, also known as rapamycin. Derivatives of sirolimus are also said to be useful as immunosuppressants. Such derivatives include, for example, Everolimus.

The side effects associated with some immunosuppressant drugs can be controlled in part by carefully controlling the level of the drug present in a patient. Because the distribution and metabolism of immunosuppressant drugs can vary greatly between patients and because of the wide range and severity of adverse reactions, accurate monitoring of the drug level (therapeutic drug monitoring or TDM) is recommended for all patients receiving immunosuppressant drugs, especially pediatric patients and those patients with hepatic impairment. TDM is also recommended when potent inducers or inhibitors of the enzyme CYP3A4 are co-administered. In addition, if sirolimus or its derivative is concomitantly administered with cyclosporine, TDM is recommended because pharmacokinetics are altered during drug co-administration. For example, if sirolimus is administered concomitantly with cyclosporin rather than administered four hours apart, sirolimus trough levels increase. For this reason, as well as to limit certain side effects, TDM should allow for better clinical results in selected cases.

Sirolimus and tacrolimus are the most important immunosuppressant drugs for organ transplantation in humans. Therapeutic monitoring of concentrations of sirolimus, tacrolimus and other related immunosuppressant drugs in blood is required to optimize dosing regimens to ensure maximal immunosuppression with minimal toxicity. Although sirolimus and tacrolimus are highly effective immunosuppressive agents, their use must be carefully managed because the effective dose range is narrow and excessive dosage can result in serious side effects. On the other hand, too little dosage of sirolimus or tacrolimus can lead to tissue rejection.

Many whole blood assays for immunosuppressant drugs such as, for example, sirolimus compounds and tacrolimus compounds, require a step using reagents to extract (release or displace) the drug from blood constituents. The chemical structures of sirolimus and tacrolimus are shown in FIG. 1. These molecules, which have a portion of their respective chemical structures in common, bind to endogenous specific binding substances such as, for example, endogenous specific binding proteins, e.g., FK-binding proteins (FKBPs). The sirolimus or tacrolimus drug molecules and drug metabolite molecules, if necessary, should be dissociated from endogenous binding substances, particularly for conducting assays for these substances. It is important to have a releasing reagent to compete with the FKBP-binding immunosuppressant drugs for binding to the endogenous binding substances and thereby release the free FKBP-binding immunosuppressant drug molecules for detection in an assay. Release of free FKBP-binding immunosuppressant drug molecules results in better assay sensitivity. Sirolimus and FK-506 ester (FKE) have been used as releasing reagents for a tacrolimus assay to release tacrolimus compounds from endogenous binding proteins. However, FK-506 ester has exhibited cross-reactivity with antibodies used in tacrolimus assays. Furthermore, the use of sirolimus as a releasing reagent is problematic because of carry-over issues where both sirolimus and tacrolimus immunoassays are carried out in the same instrument side-by-side.

There is, therefore, a continuing need to develop fast, accurate and sensitive diagnostic methods to measure levels of FKBP-binding immunosuppressant drugs in patients. The methods should employ a releasing agent for the FKBP-binding immunosuppressant drugs that has minimal cross-reactivity with a specific binding member such as, for example, an antibody, for the FKBP-binding immunosuppressant drug that is employed in an assay for the drug.

SUMMARY

Some examples in accordance with the principles described herein are directed to compositions for releasing an FKBP-binding immunosuppressant drug from endogenous binding substances in a sample suspected of containing the FKBP-binding immunosuppressant drug. The composition comprises in a buffered medium a compound of the formula I:

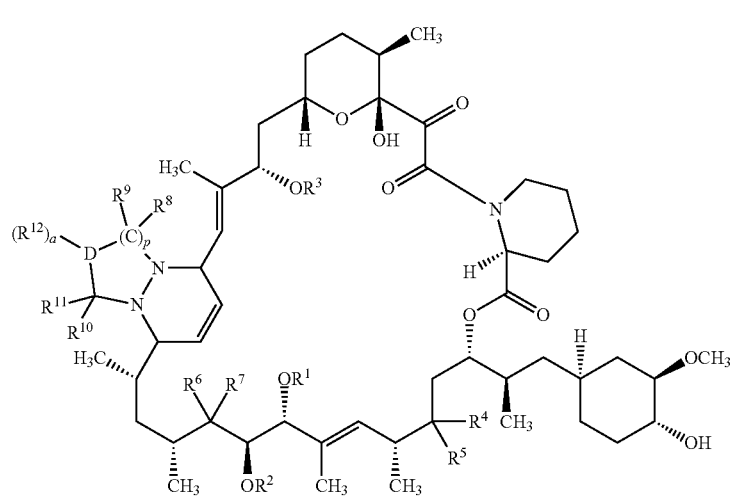

I or a compound of the formula II:

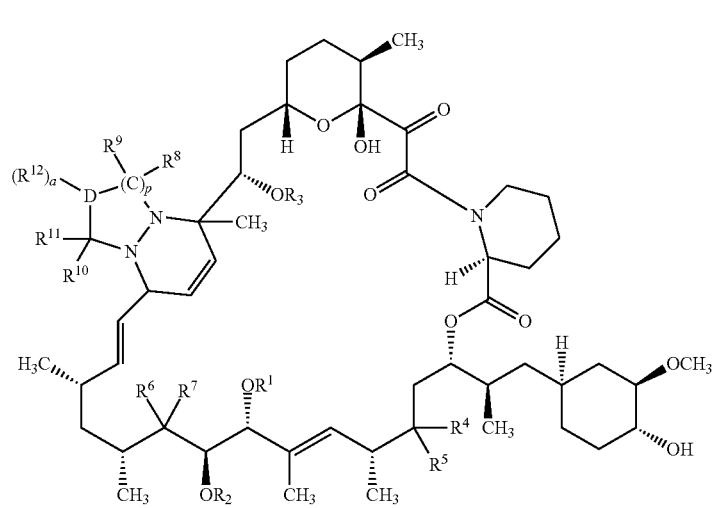

II or a mixture thereof,
wherein:
$R^1$, $R^2$ and $R^3$ are each independently H or lower alkyl;
$R^4$ and $R^5$ are each independently H, lower hydrocarbyl or lower hydrocarbyloxy or taken together to form a double bond to O, $CH_2$, N-alkyl, or N—O-alkyl;
$R^6$ and $R^7$ are each independently H, lower hydrocarbyl or lower hydrocarbyloxy or taken together to form a double bond to O, $CH_2$, N-alkyl, or N—O-alkyl;
$R^8$ and $R^9$ are each independently H, non-bulky organic radical or a bulky organic radical, or are taken together to form a double bond to O or $CH_2$;
$R^{10}$ and $R^{11}$ are each independently H, non-bulky organic radical or a bulky organic radical, or are taken together to form a double bond to O or $CH_2$;
$R^{12}$ is H, H non-bulky hydrocarbyl or a bulky organic radical;
wherein at least one of $R^8$, $R^9$, $R^{10}$, $R^{11}$ or $R^{12}$ is a bulky organic radical;
p is 1, 2 or 3;
a is 0 or 1; and
D is N, O, or CH, with the proviso that a is 0 when D is O.

In some examples in accordance with the principles described herein, the above compositions for releasing an FKBP-binding immunosuppressant drug from endogenous binding substances comprise a compound of the formula III:

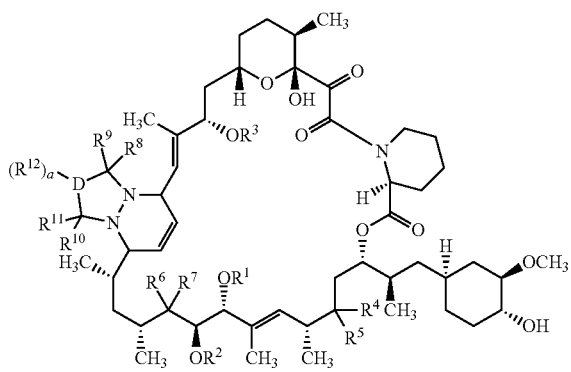

or a compound of the formula IV:

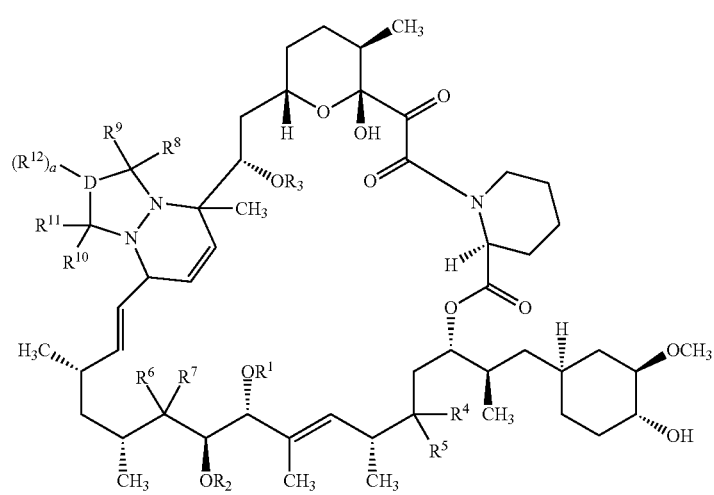

or a mixture thereof,
wherein:
$R^1$, $R^2$ and $R^3$ are each independently H or lower alkyl;
$R^4$ and $R^5$ are each independently H, lower hydrocarbyl or lower hydrocarbyloxy or taken together to form a double bond to O, $CH_2$, N-alkyl, or N—O-alkyl;

III $R^6$ and $R^7$ are each independently H, lower hydrocarbyl or lower hydrocarbyloxy or taken together to form a double bond to O, $CH_2$, N-alkyl, or N—O-alkyl;

$R^8$ and $R^9$ are each independently H, non-bulky organic radical or a bulky organic radical, or are taken together to form a double bond to O or $CH_2$;

$R^{10}$ and $R^{11}$ are each independently H, non-bulky organic radical or a bulky organic radical, or are taken together to form a double bond to O or $CH_2$;

$R^{12}$ is H, H non-bulky hydrocarbyl, or a bulky organic radical;

wherein at least one of $R^8$, $R^9$, $R^{10}$, $R^{11}$ or $R^{12}$ is a bulky organic radical;

p is 1, 2 or 3;

IV a is 0 or 1; and

D is N, O, or CH, with the proviso that a is 0 when D is O.

In some examples in accordance with the principles described herein, the above compositions for releasing an FKBP-binding immunosuppressant drug from endogenous binding substances comprise a compound of the formula V:

V

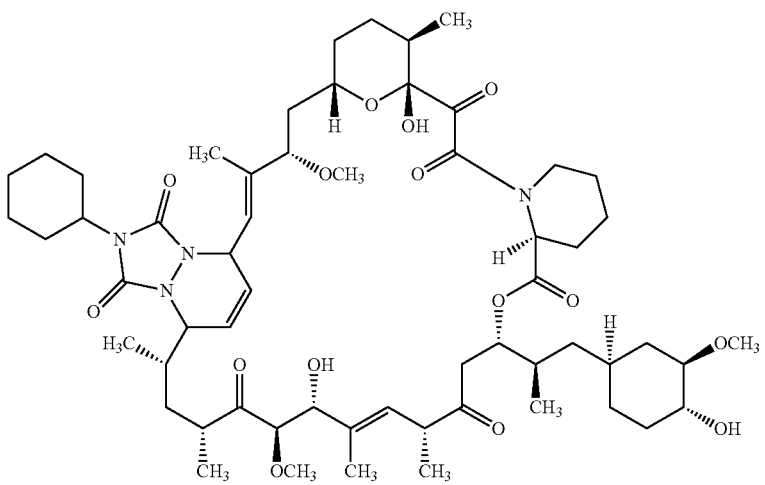

or a compound of the formula VI:

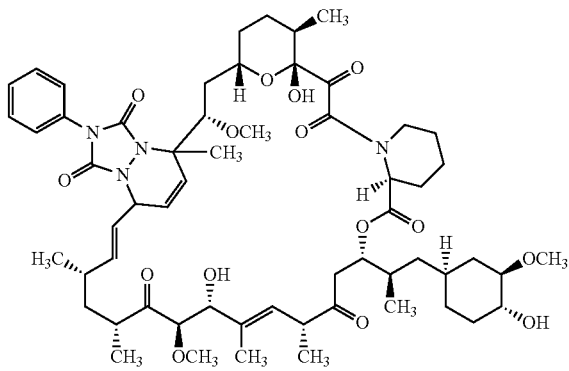

VI or a mixture thereof.

Some examples in accordance with the principles described herein are directed to methods for releasing an FKBP-binding immunosuppressant drug from endogenous binding substances in a sample suspected of containing the FKBP-binding immunosuppressant drug. A combination is provided that comprises the sample and, in an amount sufficient to release the FKBP-binding immunosuppressant drug from endogenous binding substances, a compound of the formula I:

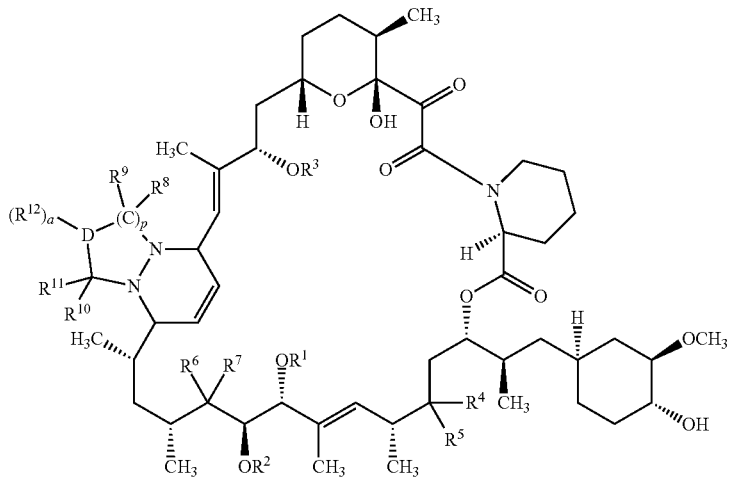

I or a compound of the formula II:

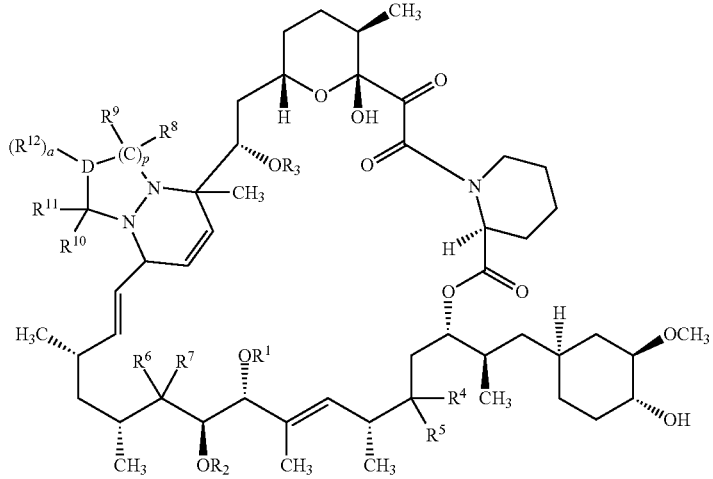

II or a mixture thereof,
wherein:
$R^1$, $R^2$ and $R^3$ are each independently H or lower alkyl;
$R^4$ and $R^5$ are each independently H, lower hydrocarbyl or lower hydrocarbyloxy or taken together to form a double bond to O, $CH_2$, N-alkyl, or N—O-alkyl;
$R^6$ and $R^7$ are each independently H, lower hydrocarbyl or lower hydrocarbyloxy or taken together to form a double bond to O, $CH_2$, N-alkyl, or N—O-alkyl;
$R^8$ and $R^9$ are each independently H, non-bulky organic radical or a bulky organic radical, or are taken together to form a double bond to O or $CH_2$;
$R^{10}$ and $R^{11}$ are each independently H, non-bulky organic radical or a bulky organic radical, or are taken together to form a double bond to O or $CH_2$;
$R^{12}$ is H, H non-bulky hydrocarbyl, or a bulky organic radical;
wherein at least one of $R^8$, $R^9$, $R^{10}$, $R^{11}$ or $R^{12}$ is a bulky organic radical;

p is 1, 2 or 3;

a is 0 or 1; and

D is N, O, or CH, with the proviso that a is 0 when D is O. The combination is incubated under conditions sufficient to release the FKBP-binding immunosuppressant drug from endogenous binding substances.

Some examples in accordance with the principles described herein are directed to methods for determining one or both of the presence and amount of an FKBP-binding immunosuppressant drug in a sample suspected of containing FKBP-binding immunosuppressant drug. In the method a combination is provided in a medium. The combination comprises the sample, and a releasing agent for releasing FKBP-binding immunosuppressant drugs from endogenous binding substances. The releasing agent is a compound of the formula I:

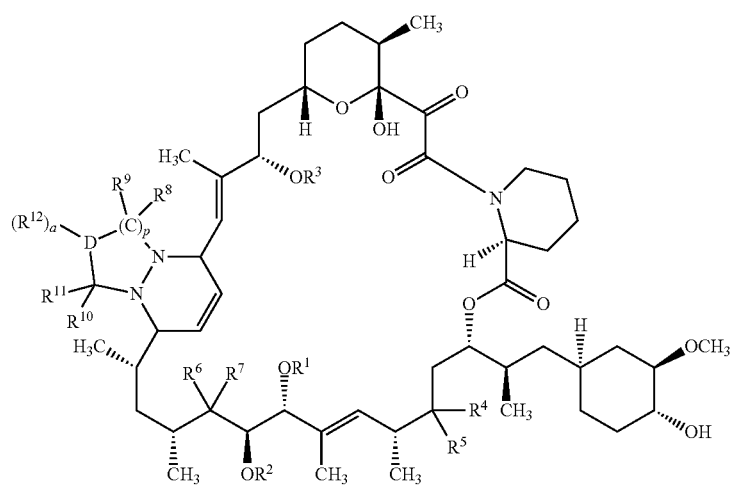

I or of the formula II:

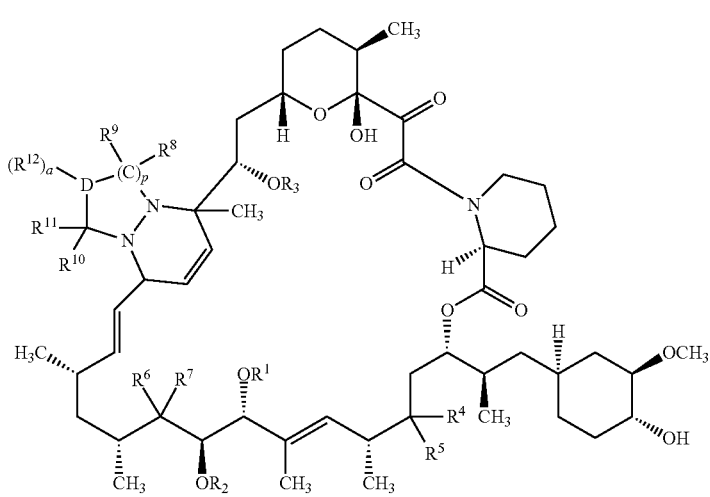

II or a mixture thereof;
wherein:

$R^1$, $R^2$ and $R^3$ are each independently H or lower alkyl;

$R^4$ and $R^5$ are each independently H, lower hydrocarbyl or lower hydrocarbyloxy or taken together to form a double bond to O, $CH_2$, N-alkyl, or N—O-alkyl;

$R^6$ and $R^7$ are each independently H, lower hydrocarbyl or lower hydrocarbyloxy or taken together to form a double bond to O, $CH_2$, N-alkyl, or N—O-alkyl;

$R^8$ and $R^9$ are each independently H, non-bulky organic radical or a bulky organic radical, or are taken together to form a double bond to O or $CH_2$;

$R^{10}$ and $R^{11}$ are each independently H, non-bulky organic radical or a bulky organic radical, or are taken together to form a double bond to O or $CH_2$;

$R^{12}$ is H, H non-bulky hydrocarbyl, or a bulky organic radical;

wherein at least one of $R^8$, $R^9$, $R^{10}$, $R^{11}$ or $R^{12}$ is a bulky organic radical;

p is 1, 2 or 3;

a is 0 or 1; and

D is N, O, or CH, with the proviso that a is 0 when D is O. The medium is incubated under conditions for releasing FKBP-binding immunosuppressant drugs from endogenous binding substances. Reagents for determining the presence and/or amount of the FKBP-binding immunosuppressant drugs in the sample are added to the medium. The reagents comprise at least one specific binding member for a FKBP-binding immunosuppressant drug. The medium is examined for the presence of a complex comprising a FKBP-binding immunosuppressant drug and the specific binding member for sirolimus or tacrolimus. The presence and/or amount of the complex is indicative of the presence and/or amount of a FKBP-binding immunosuppressant drugs in the sample.

DETAILED DESCRIPTION OF SPECIFIC EMBODIMENTS

General Discussion

Figure 1:
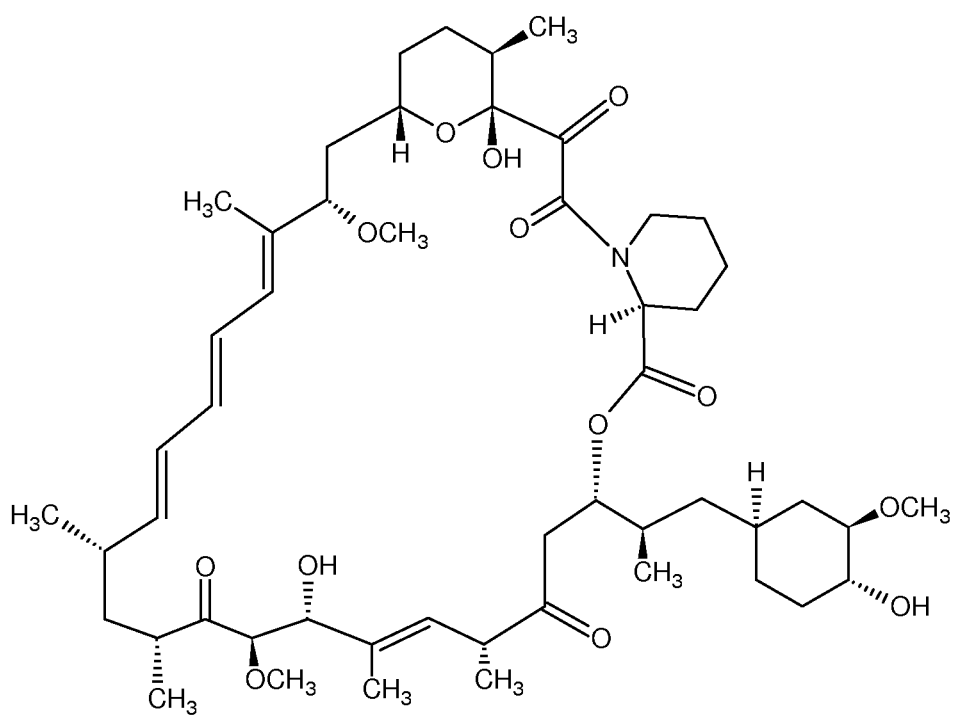
FIG. 1 is a depiction of the chemical formula of sirolimus.
Figure 2:
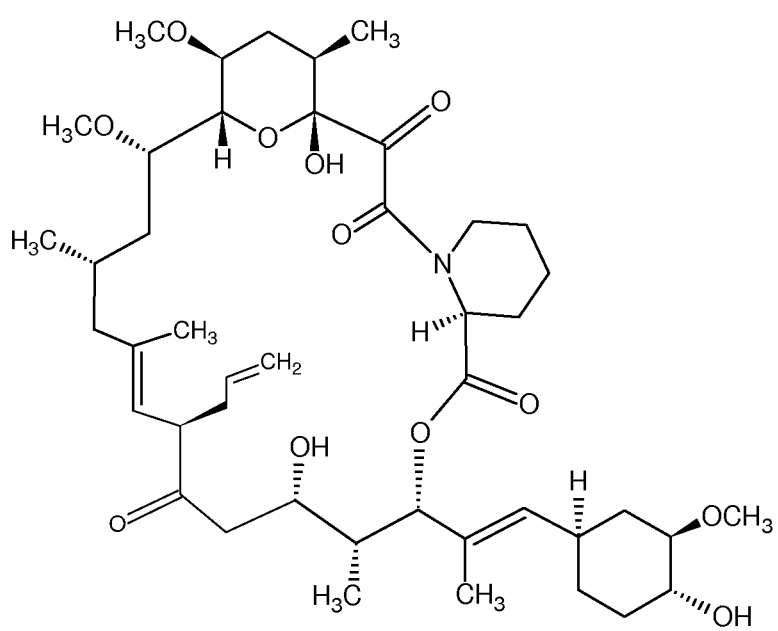
FIG. 2 is a depiction of the chemical formula of tacrolimus.

Compositions are disclosed for releasing an FKBP-binding immunosuppressant drug from endogenous binding substances in a sample suspected of containing the FKBP-binding immunosuppressant drug. The compositions include sirolimus derivatives that are modified with a bulky organic radical in the triene portion of the sirolimus molecule. The compositions may be employed in conjunction with assays for an FKBP-binding immunosuppressant drug in a sample suspected of containing the drug.

Some examples in accordance with the principles described herein are directed to compounds of formula I and formula II, to compounds of formula III and formula IV and to compounds of formula V and formula VI. The compounds may be employed to release an FKBP-binding immunosuppressant drug from endogenous binding substances that may be present in a sample. The released FKBP-binding immunosuppressant drug may then be detected in an assay for the FKBP-binding immunosuppressant drug. Compounds of the formula I, formula II, formula III, formula IV, formula V and formula VI as releasing agents exhibit minimal cross-reactivity with a specific binding member for an FKBP-binding immunosuppressant drug that is employed in such an assay. Thus, such an assay provides a more accurate determination of the presence and/or amount of an FKBP-binding immunosuppressant drug in a sample without the need for separation of the releasing agent from a medium comprising the sample prior to conducting an assay. In some examples, the releasing function and an assay may be conducted in the same medium without separation of displaced drug from a medium comprising the releasing agent.

Some examples of compounds in accordance with the principles described herein have the ability to displace more than one FKBP-binding immunosuppressant drug from endogenous binding substances. In some examples, a compound of formula I, formula II, formula III, formula IV, formula V or formula VI, or a mixture of two or more of such compounds, can be employed to displace a sirolimus compound from endogenous binding substances or to displace a tacrolimus compound from endogenous binding substances, for example. That is, in some examples, the same compound from the aforementioned compounds may be employed as a releasing agent in separate assays for two or more different FKBP-binding immunosuppressant drugs, or for three or more different FKBP-binding immunosuppressant drugs, or for four or more different FKBP-binding immunosuppressant drugs, for example. In a particular example, the same compound from the aforementioned compounds may be employed as a releasing agent in separate assays for sirolimus compounds and tacrolimus compounds.

In all of the above circumstances where the same releasing agent in accordance with the principles described herein is employed in assays for more than one FKBP-binding immunosuppressant drug, the releasing agent exhibits minimal binding or cross-reactivity with the different specific binding members employed in the assays for the different immunosuppressant drugs. The phrase "minimal binding" or "minimal cross-reactivity" means that binding of the releasing agent to the specific binding member employed in an assay for the FKBP-binding immunosuppressant drug is sufficiently low so that such binding or cross-reactivity has a negligible effect on the accuracy of the assay. The binding of the releasing agent to the specific binding member does not result in a significant increase or decrease in signal obtained in an assay for the drug. In some examples, the binding of the releasing agent to a specific binding member for the FKBP-binding immunosuppressant drug is less than about 5%, or less than about 4%, or less than about 3%, or less than about 2%, or less than about 1%, or less than about 0.5%.

The phrase "endogenous binding substances" refers to substances that originate in and are present in a sample to be analyzed where the substances bind to an FKBP-binding immunosuppressant drug. The endogenous binding substances include endogenous specific binding substances, for example, specific binding proteins such as, for example, FKBP. The term "FKBP(s)" refers to FK binding proteins or FK-506 binding proteins that include, by way of illustration and not limitation, FKBP12, immunophilins and ca acid glycoproteins, for example. The FKBPs are endogenous proteins that bind to both sirolimus compounds and tacrolimus compounds, for example.

The phase "FKBP-binding immunosuppressant drug" refers to immunosuppressant drugs that bind specifically to FKBPs including, but not limited to, FKBP12, other FKBPs, immunophilins and cd acid glycoproteins, for example. FKBP-binding immunosuppressant drugs include, but are not limited to, sirolimus compounds, which include Everolimus compounds, and tacrolimus compounds, for example.

The term "sirolimus compound(s)" as used herein includes rapamycin and its derivatives, other members of the sirolimus family and their derivatives, including, for example, esters, amides, haloacetamides and imides at one or more positions of the sirolimus molecule. Derivatives of sirolimus include, for example, Everolimus. Rapamycin derivatives include compounds containing a rapamycin nucleus, metabolites of rapamycin, and ring-opened rapamycin compounds. Rapamycin derivatives also include derivatives prepared through esterification of one or more hydroxyl groups into a carboxylic ester, a carbamate, a sulfonate ester, or an amide, for example. Rapamycin derivatives also include compounds resulting from the reduction of one or more carbonyl carbons to a hydroxyl group or reduction of one or more of the double bonds.

The term "tacrolimus compound(s)" as used herein refers to FK-506 and its derivatives, other members of the tacrolimus family and their derivatives, including, for example, esters, amides, haloacetamides and imides at one or more positions of the tacrolimus molecule. Tacrolimus derivatives include compounds containing a tacrolimus nucleus, metabolites of tacrolimus, and ring-opened tacrolimus compounds. Tacrolimus derivatives also include derivatives prepared through esterification of one or more hydroxyl groups into a carboxylic ester, a carbamate, a sulfonate ester, or an amide, for example. Tacrolimus derivatives also include compounds resulting from the reduction of one or more carbonyl carbons to a hydroxyl group or reduction of one or more of the double bonds.

The phrase "minimal cross-reactivity with a specific binding member for an FKBP-binding immunosuppressant drug" means that the releasing agent does not interfere to any significant degree with the accuracy and sensitivity of an assay for the drug by binding to the specific binding member for the drug, The binding of the releasing agent to such a specific binding member is less than about 1%, or less than about 0.5%, or less than about 0.2%, or less than about 0.1%, for example.

As mentioned above, some examples in accordance with the principles described herein are directed to compositions for releasing an FKBP-binding immunosuppressant drug from endogenous binding substances in a sample suspected of containing the FKBP-binding immunosuppressant drug. The composition comprises in a buffered medium a compound of the formula I:

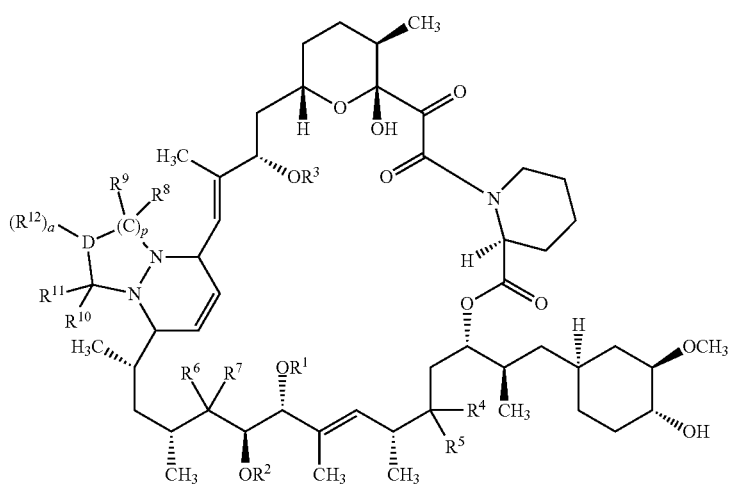

I or a compound of the formula II:

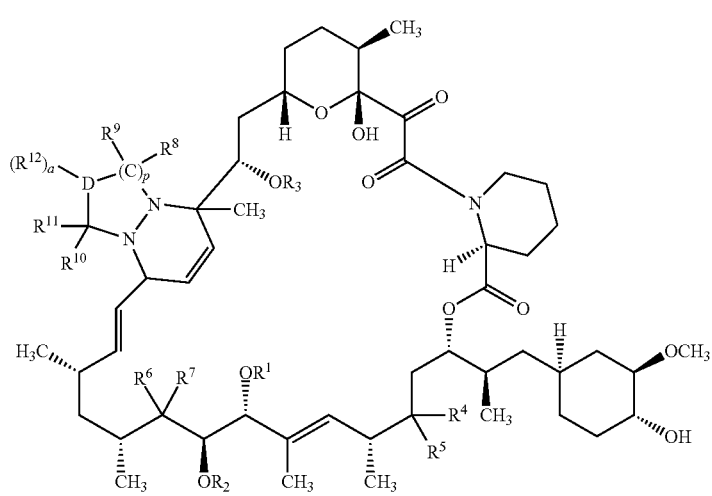

II or a mixture thereof;
wherein:
$R^1$, $R^2$ and $R^3$ are each independently H or lower alkyl;
$R^4$ and $R^5$ are each independently H, lower hydrocarbyl or lower hydrocarbyloxy or taken together to form a double bond to O, $CH_2$, N-alkyl, or N—O-alkyl;
$R^6$ and $R^7$ are each independently H, lower hydrocarbyl or lower hydrocarbyloxy or taken together to form a double bond to O, $CH_2$, N-alkyl, or N—O-alkyl;
$R^8$ and $R^9$ are each independently H, non-bulky organic radical or a bulky organic radical, or are taken together to form a double bond to O or $CH_2$;
$R^{10}$ and $R^{11}$ are each independently H, non-bulky organic radical or a bulky organic radical, or are taken together to form a double bond to O or $CH_2$;
$R^{12}$ is H, H non-bulky hydrocarbyl, or a bulky organic radical;
wherein at least one of $R^8$, $R^9$, $R^{10}$, $R^{11}$ or $R^{12}$ is a bulky organic radical;
p is 1, 2 or 3;
a is 0 or 1; and
D is N, O, or CH, with the proviso that a is 0 when D is O.

The term "hydrocarbyl" refers to an organic radical that consists solely of carbon and hydrogen. A hydrocarbyl group may be unsaturated or it may contain one or more carbon-carbon double bonds or one or more carbon-carbon triple bonds or a mixture thereof. The term "hydrocarbyl" includes alkyl, alkenyl and alkynyl.

The phrase "bulky organic radical" refers to an organic radical that exhibits a large molecular size for its weight. The bulky organic radical hinders the ability of a specific binding member to bind to an area of a molecule that comprises the bulky organic radical. The phrase "bulky hydrocarbyl" refers to a hydrocarbyl group that exhibits a large molecular size for its weight such as, for example, that exhibited by an alkyl group that is branched or cyclic.

The phrase "non-bulky organic radical" refers to an organic radical that does not exhibit a large molecular size for its weight. The non-bulky organic radical does not hinder to a significant degree the ability of an antibody to bind to an area of a molecule that comprises the non-bulky organic radical. The phrase "non-bulky hydrocarbyl" refers to a hydrocarbyl group that does not exhibit a large molecular size for its weight such as that exhibited by a straight chain alkyl group.

The term "alkyl" refers to an organic radical that consists solely of single-bonded carbon and hydrogen in either a straight, branched, or cyclic configuration. The number of carbon atoms in the organic radical is 1 to 50, or 1 to 40, or 1 to 30, or 1 to 25, or 1 to 20, or 1 to 15, or 1 to 10, or 1 to 5, or 2 to 50, or 2 to 40, or 2 to 30, or 2 to 25, or 2 to 20, or 2 to 15, or 2 to 10, or 2 to 5, or 5 to 50, or 5 to 40, or 5 to 30, or 5 to 25, or 5 to 20, or 5 to 15, or 5 to 10. The term "lower alkyl" refers to alkyl wherein the number of carbon atoms in the organic radical is 1 to 10, or 1 to 9, or 1 to 8, or 1 to 7, or 1 to 6, or 1 to 5, or 1 to 4, or 1 to 3, or 1 to 2, or 2 to 10, or 2 to 9, or 2 to 8, or 2 to 7, or 2 to 6, or 2 to 5, or 2 to 4, or 2 to 3, or 3 to 10, or 3 to 9, or 3 to 8, or 3 to 7, or 3 to 6, or 3 to 5, or 3 to 4, or 4 to 10, or 4 to 9, or 4 to 8, or 4 to 7, or 4 to 6, or 4 to 5, or 5 to 10, or 5 to 9, or 5 to 8, or 5 to 7, or 5 to 6, or 6 to 10, or 6 to 9, or 6 to 8, or 6 to 7, or 7 to 10, or 7 to 9, or 7 to 8, or 8 to 10, or 8 to 9, or 9 to 10.

Bulky hydrocarbyl includes branched chain hydrocarbyl and cyclic hydrocarbyl. Bulky branched chain hydrocarbyl has branching at or near the carbon atom that is attached to another molecule. Examples of bulky branched chain alkyl include, but are not limited to, sec-butyl, tert-butyl, triethylmethyl, diethylmethyl, tripropylmethyl and dipropylmethyl, for example. Cyclic alkyl is alkyl comprising one or more rings. Examples of cyclic alkyl include, but are not limited to, cyclopropyl, cyclobutyl, cyclopentyl, cyclohexyl, cycloheptyl and norbornyl, for example. Examples of non-bulky alkyl include, but are not limited to, methyl, ethyl, propyl, butyl, pentyl, hexyl, heptyl and octyl, for example.

The term "alkenyl" refers to a hydrocarbyl group having hydrocarbon chains of the number of carbon atoms specified above of either a straight- or branched-configuration and having at least one carbon-carbon double bond, which may occur at any point along the hydrocarbon chain, examples of which include, but are not limited to, ethenyl, propenyl, butenyl, pentenyl, dimethyl pentenyl, for example.

The term "alkynyl" refers to a hydrocarbyl group having hydrocarbon chains of the number of carbon atoms specified above containing at least one carbon-carbon triple bond, including, but not limited to, ethynyl, 1-propynyl, 2-propynyl, 1-butynyl, and 2-butynyl, for example.

The term "lower hydrocarbyloxy" refers to a hydrocarbyl group that is an organic radical of the number of carbon atoms designated above of either a straight, branched or cyclic configuration wherein the organic radical includes an ether oxygen for linking a hydrocarbyl group to a parent compound.

The term "lower alkoxy" refers to an organic radical of the number of carbon atoms designated above of either a straight, branched or cyclic configuration wherein the organic radical includes an ether oxygen for linking an alkyl group to a parent compound.

As used herein, the term "aryl" refers to an organic radical derived from an aromatic hydrocarbon by the removal of one atom and containing one or more aromatic rings such as, but not limited to, 1 to 5 aromatic rings, or 1 to 4 aromatic rings, or 1 to 3 aromatic rings, or 1 to 2 aromatic rings, or 2 to 4 aromatic rings, or 2 to 3 aromatic rings, for example. Examples of aryl include, but are not limited to, phenyl (from benzene), naphthyl (from naphthalene), and anthracyl (from anthracene), for example. The aryl radical may be substituted or unsubstituted. "Substituted aryl" refers to aryl groups that comprise one or more substituents such as, but not limited to, a bulky hydrocarbyl, a non-bulky hydrocarbyl, a functional group (e.g., chloro, bromo, iodo, fluoro, nitro and sulfone), for example.

As used herein, "arylhydrocarbyl" refers to an organic radical having a lower hydrocarbyl group to which is attached an aryl group. As used herein, "aralkyl" refers to an organic radical having a lower alkyl group to which is attached an aryl group such as, but not limited to, benzyl, phenethyl, 3-phenylpropyl and 1-naphthylethyl, for example.

In some examples in accordance with the principles described herein, $R^1$, $R^2$ and $R^3$ are each independently H or methyl or ethyl. In some examples in accordance with the principles described herein, $R^4$ and $R^5$ are each independently H, methyl, ethyl, methoxy, ethoxy or taken together to form a double bond to O. In some examples in accordance with the principles described herein, $R^6$ and $R^7$ are each independently H, methyl, ethyl, methoxy, ethoxy or taken together to form a double bond to O. In some examples in accordance with the principles described herein, $R^8$ and $R^9$ are each independently H, methyl, ethyl, methoxy, ethoxy or taken together to form a double bond to O. In some examples in accordance with the principles described herein, $R^{10}$ and $R^{11}$ are each independently H, methyl, ethyl, methoxy, ethoxy or taken together to form a double bond to O. In some examples in accordance with the principles described herein, $R^{12}$ is H, tert-butyl, phenyl or benzyl. In some examples in accordance with the principles described herein, a is 1 and D is N.

Some examples in accordance with the principles described herein are directed to compositions for releasing an FKBP-binding immunosuppressant drug from endogenous binding substances in a sample suspected of containing the FKBP-binding immunosuppressant drug where the composition comprises in a buffered medium a compound of the formula III:

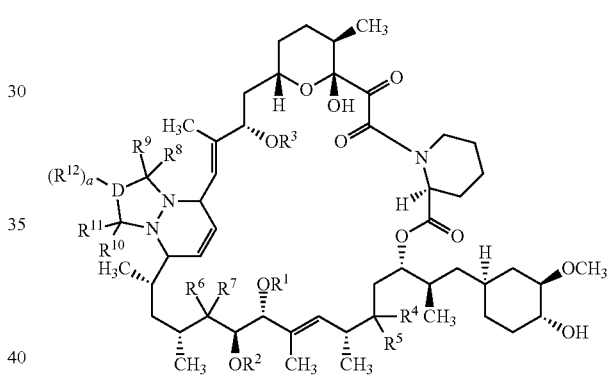

or a compound of the formula IV:

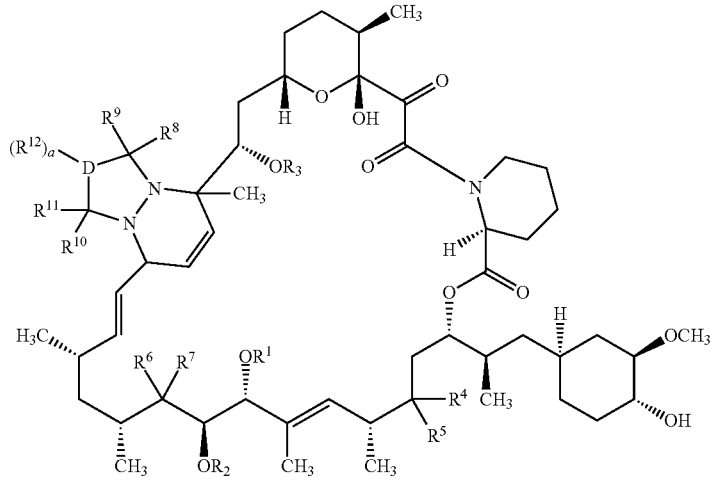

or a mixture of compounds of formula III and formula IV, wherein:
$R^1$, $R^2$ and $R^3$ are each independently H or lower alkyl;
$R^4$ and $R^5$ are each independently H, lower hydrocarbyl or lower hydrocarbyloxy or taken together to form a double bond to O, $CH_2$, N-alkyl, or N—O-alkyl;
$R^6$ and $R^7$ are each independently H, lower hydrocarbyl or lower hydrocarbyloxy or taken together to form a double bond to O, $CH_2$, N-alkyl, or N—O-alkyl;
$R^8$ and $R^9$ are each independently H, non-bulky organic radical or a bulky organic radical, or are taken together to form a double bond to O or $CH_2$;
$R^{10}$ and $R^{11}$ are each independently H, non-bulky organic radical or a bulky organic radical, or are taken together to form a double bond to O or $CH_2$;
$R^{12}$ is H, H non-bulky hydrocarbyl, or a bulky organic radical; wherein at least one of $R^8$, $R^9$, $R^{10}$, $R^{11}$ or $R^{12}$ is a bulky organic radical;
p is 1, 2 or 3;
a is 0 or 1; and
D is N, O, or CH, with the proviso that a is 0 when D is O.

In some examples in accordance with the principles described herein, a composition comprises in a buffered medium a compound of the formula V:

In some examples in accordance with the principles described herein, a composition for use as a releasing agent for an FKBP-binding immunosuppressant drug includes a mixture of compounds of formula V and formula VI.

Preparation of Compounds

Figure 3:
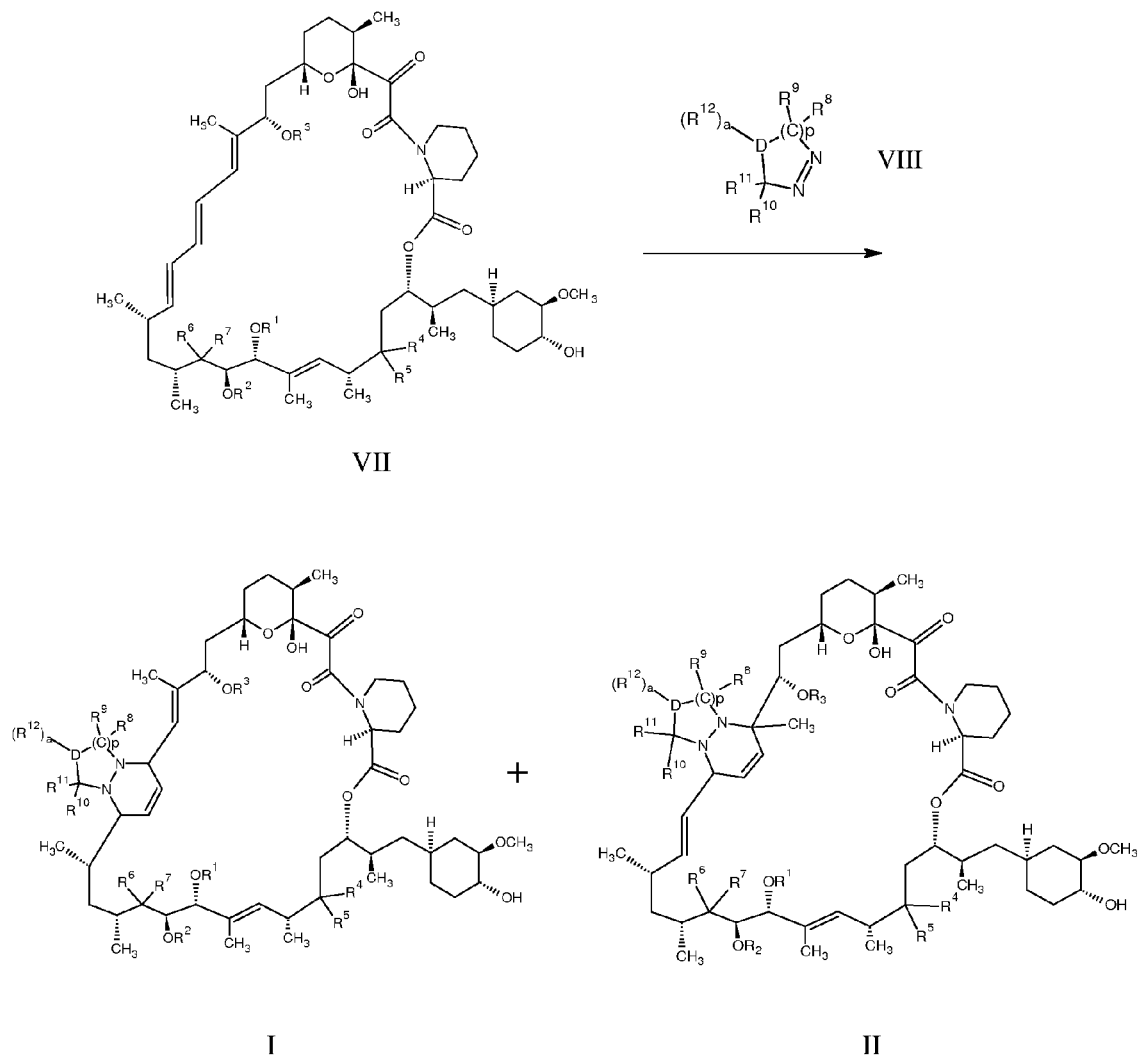
FIG. 3 is a schematic diagram of a synthesis of compounds employed in the compositions and methods in accordance with examples in accordance with the principles described herein.

Examples of methods of preparing compounds in accordance with the principles described herein are described, by way of illustration and not limitation, with reference to FIG. 3. Other approaches may be employed to form the compounds consistent with the principles described herein. Referring to FIG. 3, sirolimus compound VII is combined with cyclic reagent VIII under conditions for carrying out a Diels-Alder addition reaction. The conditions include using an anhydrous non-polar organic medium such as, but not limited to, methylene chloride, toluene, hexane, nitrobenzene and carbon tetrachloride, for example; or a polar organic medium such as, but not limited to, ethanol, acetonitrile and phosphonium tosylates, and aqueous mixtures thereof, for example. The reaction is conducted at a temperature of about 15° C. to about 40° C., or about 20° C. to about 30° C., or about room temperature (about 22° C. to about 24° C.) for a period of about 15 minutes to about 45 minutes or about 30 minutes and

V

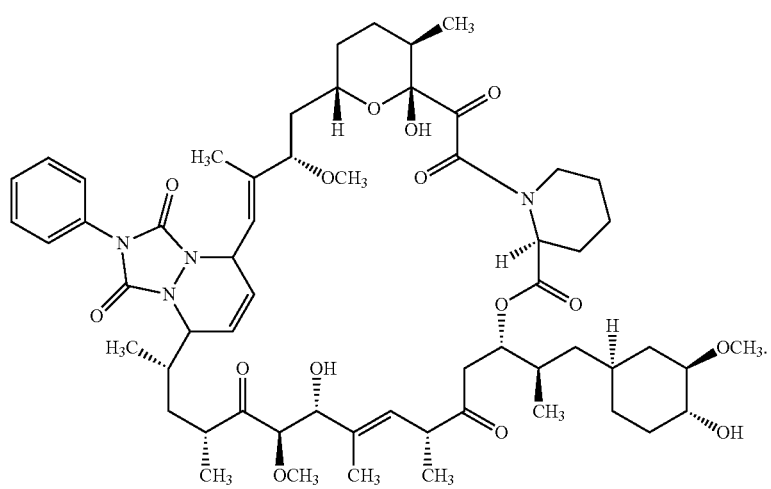

In some examples in accordance with the principles described herein, a composition comprises a compound of the formula VI:

VI

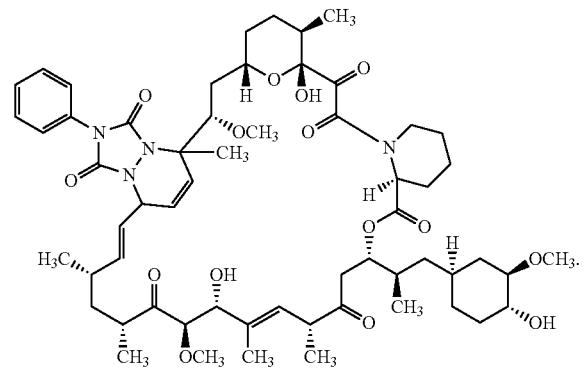

then at a temperature of about 50° C. to about 100° C., or about 50° C. to about 80° C., or about the reflux temperature of the non-polar organic solvent for a period of about 30 minutes to about 90 minutes, or about 45 minutes to about 75 minutes, or about 60 minutes. The resulting product is purified by one or more techniques such as, but not limited to, evaporation, recrystallization, and chromatography such as, for example, thin layer chromatography (TLC), high performance liquid chromatography (HPLC), reverse phase liquid chromatography (RPLC), high turbulence liquid chromatography (HTLC), gas chromatography, for example. The product is a mixture of two isomers represented by compounds I and II in FIG. 3, which may be employed together or may be separated by one or more techniques for separating positional isomers such as, but not limited to, chromatography (TLC, HPLC, RPLC, HTLC), and gas chromatography, for example.

Figure 4:
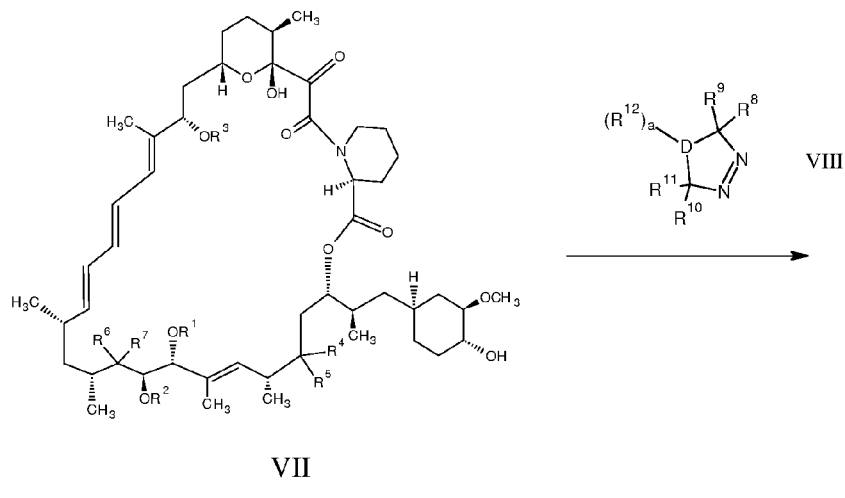
FIG. 4 is a schematic diagram of a synthesis of compounds employed in the compositions and methods in accordance with examples in accordance with the principles described herein.
Figure 4:
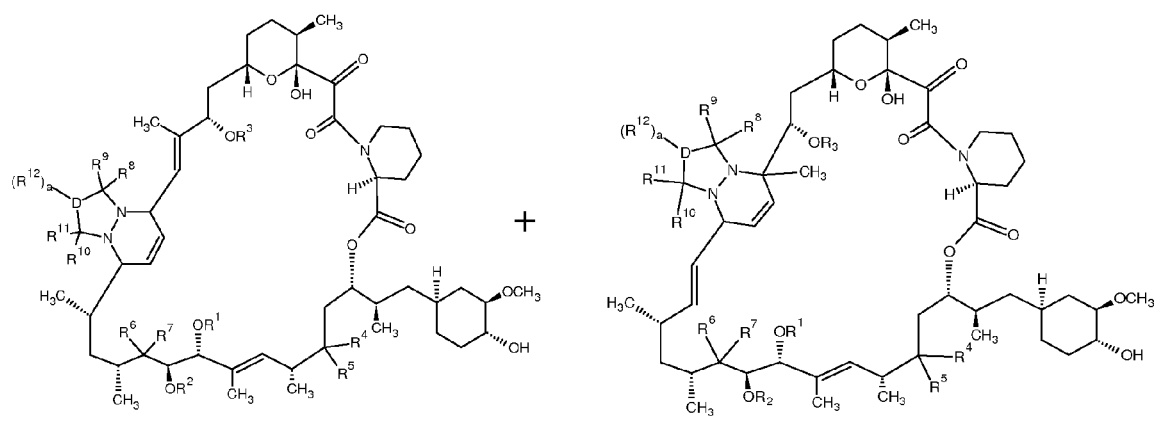

Another example of a preparation of examples of compounds in accordance with the principles described herein is illustrated in FIG. 4. Referring to FIG. 4, sirolimus compound VII is combined with cyclic reagent VIII under conditions for carrying out a Diels-Alder addition reaction similar to those described above to produce compounds III and IV.

Figure 5:
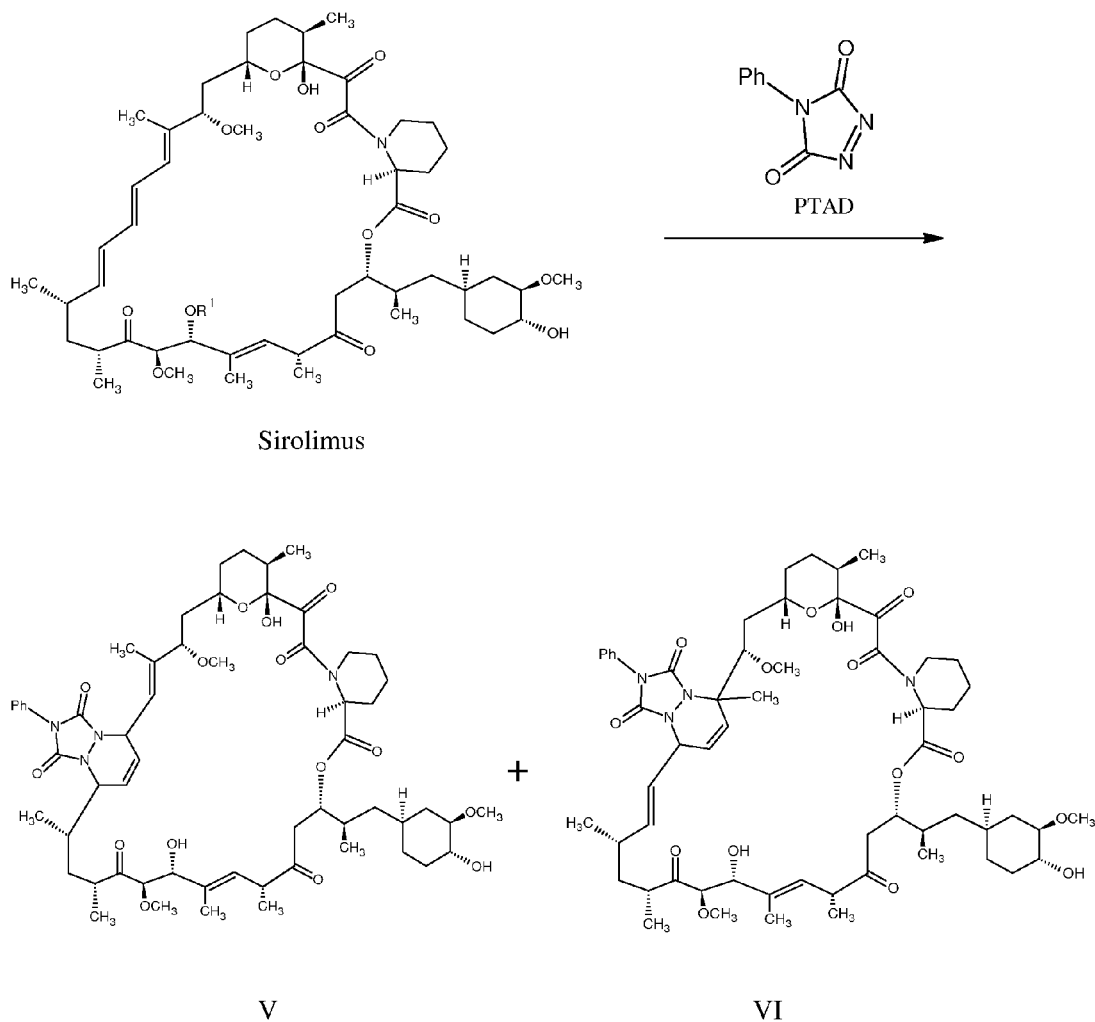
FIG. 5 is a schematic diagram of a synthesis of compounds employed in the compositions and methods in accordance with examples in accordance with the principles described herein.

A particular example of a method of preparing compounds in accordance with the principles described herein is described, by way of illustration and not limitation, with reference to FIG. 5. Other approaches may be employed to form the compounds consistent with the principles described herein. Referring to FIG. 5, sirolimus is combined with cyclic reagent PTAD under conditions for carrying out a Diels-Alder addition reaction. The conditions include using an anhydrous non-polar organic medium such as, but not limited to, methylene chloride, toluene, hexane, nitrobenzene and carbon tetrachloride, for example; or a polar organic medium such as, but not limited to, ethanol, acetonitrile and phosphonium tosylates, and aqueous mixtures thereof, for example. The reaction is conducted at a temperature of about 15° C. to about 40° C., or about 20° C. to about 30° C., or about room temperature (about 22° C. to about 24° C.) for a period of about 15 minutes to about 45 minutes or about 30 minutes and then at a temperature of about 50° C. to about 100° C., or about 50° C. to about 80° C., or about the reflux temperature of the non-polar organic solvent for a period of about 30 minutes to about 90 minutes, or about 45 minutes to about 75 minutes, or about 60 minutes. The resulting product is purified by one or more techniques such as, but not limited to, evaporation, chromatography such as, for example, thin layer chromatography (TLC), high performance liquid chromatography (HPLC), reverse phase liquid chromatography (RPLC), high turbulence liquid chromatography (HTLC) and gas chromatography, for example. The product is a mixture of two isomers represented by compounds V and VI in FIG. 5, which may be employed together or may be separated by one or more techniques for separating positional isomers such as, but not limited to, chromatography (TLC, HPLC, RPLC, HTLC) and gas chromatography, for example.

Use of Compounds as Releasing Agents

As mentioned above, some examples in accordance with the principles described herein are directed to methods for releasing an FKBP-binding immunosuppressant drug from endogenous binding substances in a sample suspected of containing one or more FKBP-binding immunosuppressant drugs. A combination is provided that comprises the sample and, as a pretreatment releasing reagent, one of the aforementioned compounds in an amount sufficient to release FKBP-binding immunosuppressant drugs from endogenous binding substances.

The sample to be tested may be non-biological or biological. "Non-biological samples" are those that do not relate to a biological material and include, for example, soil samples, water samples, air samples, samples of other gases and mineral samples. The phrase "biological sample" refers to any biological material such as, for example, body fluid, body tissue, body compounds and culture media. The sample may be a solid, semi-solid or a fluid (a liquid or a gas) from any source. In some embodiments the sample may be a body excretion, a body aspirant, a body excisant or a body extractant. The body may be mammalian or non-mammalian. In some examples, the body is a human body. Body excretions are those substances that are excreted from a body (although they also may be obtained by excision or extraction) such as, for example, urine, feces, stool, vaginal mucus, semen, tears, breath, sweat, blister fluid and inflammatory exudates. Body excisants are those materials that are excised from a body such as, for example, skin, hair and tissue samples including biopsies from organs and other body parts. Body aspirants are those materials that are aspirated from a body such as, for example, mucus, saliva and sputum. Body extractants are those materials that are extracted from a body such as, for example, whole blood, plasma, serum, spinal fluid, cerebral spinal fluid, lymphatic fluid, synovial fluid and peritoneal fluid.

For releasing of the FKBP-binding immunosuppressant drug, the sample can be prepared in any convenient medium that does not interfere with an assay; an aqueous medium generally is employed and in some examples the medium is the medium in which an assay is subsequently or concomitantly carried out. The size of the sample portion is dependent on one or more of the nature of the sample, the nature of the FKBP-binding immunosuppressant drug, the nature of the assay, the nature of the various reagents for conducting the assay, and the nature of the complex comprising the FKBP-binding immunosuppressant drug, for example. In some embodiments the volume of the sample portion is about 1 µL to about 100 µL, or about 2 µL to about 100 µL, or about 5 µL to about 100 µL, or about 10 µL to about 100 µL, or about 1 µL to about 80 µL, or about 1 µL to about 60 µL, or about 1 µL to about 40 µL, or about 1 µL to about 20 µL, or about 5 µL to about 50 µL, or about 10 µL to about 50 µL, for example.

The concentration of the releasing agent in the medium is that which is sufficient to achieve the desired result of displacing substantially all of the FKBP-binding immunosuppressant drug, and in some instances metabolites of the FKBP-binding immunosuppressant drug, from endogenous binding substances to render the FKBP-binding immunosuppressant drug, and metabolites if desired, accessible for binding to a specific binding member for the FKBP-binding immunosuppressant drug and metabolites. The phrase "displace substantially all of the FKBP-binding immunosuppressant drug that is bound by endogenous binding substances" means that the FKBP-binding immunosuppressant drug is at least 80%, or at least 85%, or at least 90%, or at least 95%, or at least 99%, or at least 99.5%, or at least 99.9% or is 100% displaced from endogenous binding substances and available for detection during an assay. The amount or concentration of releasing agent employed depends on one or more of the nature of the sample, the nature of the FKBP-binding immunosuppressant drug, the nature of metabolites of the FKBP-binding immunosuppressant drug, the nature of other reagent components, and the reaction conditions, for example. In some examples the amount of the releasing agent is about 0.000001% to about 0.5%, about 0.0001% to about 0.4%, about 0.001% to about 0.3%, about 0.01% to about 0.2%, about 0.1% to about 0.3%, about 0.2% to about 0.5%, about 0.1% to about 0.2%, and so forth (percent is weight/volume).

After addition of the releasing agent, the medium comprising the sample is incubated for a period of time under conditions to displace substantially all of the FKBP-binding immunosuppressant drug, and metabolites if desired, from endogenous binding substances. The length and conditions of the incubation are dependent on one or more of the nature of the releasing agent, the nature of the FKBP-binding immunosuppressant drug, and the suspected concentration of the FKBP-binding immunosuppressant drug, for example. In some embodiments incubation temperatures for this step may be about 5° C. to about 99° C., or about 15° C. to about 70° C., or about 20° C. to about 45° C., for example. The time period for the incubation is about 0.2 seconds to about 24 hours, or about 1 second to about 6 hours, or about 2 seconds to about 1 hour, or about 1 to about 15 minutes, for example. As mentioned above, the incubation may be carried out in a medium that, for convenience, may be an assay medium as discussed herein, but need not be.

A compound in accordance with the principles described herein may be added directly to a medium comprising a sample aliquot. On the other hand, a compound in accordance with the principles described herein may be included in a pretreatment reagent solution and the sample aliquot added to the pretreatment reagent solution. In either instance the medium comprising the sample or the pretreatment reagent solution itself may comprise one or more of a hemolytic agent, a buffer, an anti-clotting agent, and a preservative, for example. The above agents, if utilized, are present in an amount sufficient to achieve the desired effect or function.

When a separate pretreatment reagent solution is prepared, it is formulated in an aqueous medium that may be solely water or that may contain about 0.1% to about 40%, or about 0.1% to about 30%, or about 0.1% to about 20%, or about 0.1% to about 10%, or about 0.1% to about 5%, or about 0.5% to about 5%, of a polar organic solvent such as, but not limited to, an alcohol or an ether, for example.

In some embodiments a hemolytic agent is employed, which is an agent that disrupts cellular membranes in which the FKBP-binding immunosuppressant drug may be entrapped. For example, an FKBP-binding immunosuppressant drug that is entrapped within red blood cells may be released from the red blood cells by employing a hemolytic agent. A hemolytic agent is a compound or mixture of compounds that disrupt the integrity of the membranes of red blood cells thereby displacing intracellular contents of the cells and, in particular, erythrocytes. Numerous hemolytic agents are known in the art. Hemolytic agents include, for example, non-ionic detergents, anionic detergents, amphoteric detergents, low ionic strength aqueous solutions (hypotonic solutions), bacterial agents, and antibodies that cause complement dependent lysis. The hemolytic agent is present in an amount of about 0.01% to about 20%, or about 0.1% to about 20%, or about 0.5% to about 20%, or about 0.01% to about 10%, or about 0.1% to about 10%, or about 0.5% to about 10%, or about 0.01% to about 5%, or about 0.1% to about 5%, or about 0.5% to about 5%, or about 0.01% to about 1%, or about 0.1% to about 1%, or about 0.5% to about 1%, or about 0.01% to about 0.5%, or about 0.1% to about 0.5%, for example.

Non-ionic detergents that may be employed as the hemolytic agent include both synthetic detergents and natural detergents. Examples of synthetic detergents include TRITON™ X-100, TRITON™ N-101, TRITON™ X-114, TRITON™ X-405, TRITON™ SP-135, TWEEN® 20 (polyoxyethylene (20) sorbitan monolaurate), TWEEN® 80 (polyoxyethylene (20) sorbitan monooleate), DOWFAX®, ZONYL®, pentaerythrityl palmitate, ADOGEN® 464, ALKANOL® 6112 surfactant, allyl alcohol 1,2-butoxylate-block-ethoxylate HLB 6, BRIJ®, ethylenediamine tetrakis (ethoxylate-block-propoxylate) tetrol, IGEPAL®, MERPOL®, poly(ethylene glycol), 2-[ethyl[(heptadecafluorooctyl)sulfonyl]amino]ethyl ether, polyethylene-block-poly(ethylene glycol), polyoxyethylene sorbitan tetraoleate, polyoxyethylene sorbitol hexaoleate, TERGITOL® NP-9, GAFAC® (RHODAFAC®, an alkyl polyoxyethylene glycol phosphate ester such as, for example, alpha-dodecyl-omega-hydroxypoly(oxy-1,2-ethanediyl) phosphate), and EP110® and the like. Naturally-occurring detergents that may be employed as the hemolytic agent include, for example, saponins, sodium or potassium neutralized fatty acid, neutralized phospholipids, diacylglycerol, neutralized phosphatidyl serine, phosphatidate, neutralized phosphatidyl ethanolamine, phosphatidyl choline, phosphatidyl inositol, phosphatidylcholine, bile salt, unesterified cholesterol, neutralized sphingosine, ceramide, and the like. Combinations of one or more synthetic detergents or one or more naturally occurring detergents or combinations of synthetic detergents and naturally occurring detergents may also be employed.

A buffer, if employed in the medium or in a pretreatment reagent solution, may be a buffer that is employed in an assay for an analyte. Illustrative buffers include, but are not limited to, borate, phosphate, carbonate, Tris, barbital, PIPES, HEPES, MES, ACES, MOPS and BICINE, for example. The pH for the assay medium or for the pretreatment reagent solution will be in the range of about 4 to about 11, or in the range of about 5 to about 10, or in the range of about 6.5 to about 9.5, for example. The pH will usually be a compromise between that required for an assay and that required for achieving release or displacement of an FKBP-binding immunosuppressant drug from endogenous binding substances, for example.

The medium may also comprise agents for preventing the formation of blood clots. Such agents include, but are not limited to, ethylenediamine tetraacetate (EDTA), ethylene glycol tetraacetate (EGTA), citrate and heparin, for example. The anti-blood clotting agent is present in an amount of about 0.05% to about 10%, or about 0.1% to about 10%, or about 0.05% to about 5%, or about 0.1% to about 5%, or about 0.05% to about 1%, or about 0.1% to about 1%, or about 0.05% to about 0.5%, or about 0.1% to about 0.5%, or.

Other agents that may be employed in the pretreatment reagent solution include solubility reagents such as, for example, a small amount of an organic solvent such as, e.g., methanol, ethanol, isopropanol, methoxy propanol and dimethylsulfoxide (DMSO); and agents for carrying out protein digestion such as, for example, proteinases, trypsin, pepsin, and peptidases; for example. As mentioned above, any of the above agents are present in a concentration sufficient to achieve that desired effect or function.

General Description of Assays for an Analyte

Any suitable assay may be employed for determining one or both of the presence and amount of an FKBP-binding immunosuppressant drug. The assays may be conducted on the sample as an immediate continuation of the treatment of the sample with a releasing agent as discussed above or the assay may be carried out at a point thereafter. The assays are conducted by combining in an assay medium the sample with reagents for determining the amount of the FKBP-binding immunosuppressant drug in the sample. The nature of the reagents is dependent on the particular type of assay to be performed. The combination in the medium is subjected to conditions for binding of the FKBP-binding immunosuppressant drug to a specific binding member for the drug to form a complex. The amount of the complex is measured where the amount of the complex is related to one or both of the presence and amount of FKBP-binding immunosuppressant drug in the sample.

As indicated above, in many embodiments the reagents comprise at least one specific binding member for the FKBP-binding immunosuppressant drug. The specific binding member is a member of a specific binding pair (sbp member), which is one of two different molecules, having an area on the surface or in a cavity, which specifically binds to and is thereby defined as complementary with a particular spatial and polar organization of the other molecule. The members of the specific binding pair will usually be members of an immunological pair such as antigen-antibody, although other specific binding pairs such as biotin-avidin, hormones-hormone receptors, enzyme-substrate, nucleic acid duplexes, IgG-protein A, polynucleotide pairs such as DNA-DNA, DNA-RNA, for example, are not immunological pairs but are included within the scope of the term "specific binding member" or "sbp member."

Specific binding involves the specific recognition of one of two different molecules for the other compared to substantially less recognition of other molecules. On the other hand, non-specific binding involves non-covalent binding between molecules that is relatively independent of specific surface structures. Non-specific binding may result from several factors including hydrophobic interactions between molecules.

As mentioned above, releasing agents in accordance with the principles described herein exhibit minimal cross-reactivity with a specific binding member such as, for example, an antibody, for an FKBP-binding immunosuppressant drug that is employed in such an assay. Moreover, as discussed above, in the circumstance where the same releasing agent in accordance with the principles described herein is employed in assays for more than one FKBP-binding immunosuppressant drug, the releasing agent exhibits minimal binding or cross-reactivity with the different specific binding members employed in the assays for the different immunosuppressant drugs.

In some examples of assays in accordance with the principles described herein, the specific binding member for the FKBP-binding immunosuppressant drug is an antibody for the FKBP-binding immunosuppressant drug, which may be a complete immunoglobulin molecule or a fragment thereof. Antibodies include various classes and isotypes, such as IgA, IgD, IgE, IgG1, IgG2a, IgG2b and IgG3, and IgM, for example. Fragments thereof may include Fab, Fv and F(ab')$_2$, Fab', and the like. In addition, aggregates, polymers, and conjugates of immunoglobulins or their fragments can be used where appropriate so long as binding affinity for the FKBP-binding immunosuppressant drug is retained. Antibodies for the FKBP-binding immunosuppressant drug may be prepared by techniques including, but not limited to, immunization of a host and collection of sera (polyclonal), preparing continuous hybrid cell lines and collecting the secreted protein (monoclonal) or cloning and expressing nucleotide sequences or mutagenized versions thereof coding at least for the amino acid sequences required for specific binding of natural antibodies, for example.

In general, the assay is a method of determining an amount of an FKBP-binding immunosuppressant drug in a sample. The assay may be an immunoassay or a non-immunoassay. Various assay methods are discussed below by way of illustration and not limitation. An antibody selected for use in an immunoassay for an analyte, for example, should specifically and preferentially bind the analyte (and its pharmaceutically active metabolites, if necessary or desired) over other ligands such as other metabolites or related substances.

An assay for FKBP-binding immunosuppressant drug can be performed either without separation (homogeneous) or with separation (heterogeneous) of any of the assay components or products. Heterogeneous assays usually involve one or more separation steps. The assays can be competitive or non-competitive. Immunoassays may involve labeled or non-labeled reagents. Immunoassays involving non-labeled reagents usually comprise the formation of relatively large complexes involving one or more antibodies prepared from immunogenic conjugates in accordance with the principles described herein. Such assays include, for example, immunoprecipitin and agglutination methods and corresponding light scattering techniques such as, e.g., nephelometry and turbidimetry, for the detection of antibody complexes. Labeled immunoassays include, but are not limited to, chemiluminescence immunoassays, enzyme immunoassays, fluorescence polarization immunoassays, radioimmunoassays, inhibition assays, induced luminescence assays, and fluorescent oxygen channeling assays, for example.

One general group of immunoassays that may be employed includes immunoassays using a limited concentration of antibody. Another group of immunoassays involves the use of an excess of one or more of the principal reagents such as, for example, an excess of an antibody for the analyte. Another group of immunoassays includes separation-free homogeneous assays in which a labeled reagent in accordance with the principles described herein modulates the label signal upon binding of a compound in accordance with the principles described herein to a specific binding member for an FKBP-binding immunosuppressant drug, thus competing with FKBP-binding immunosuppressant drug that may be present in the sample. Other reagents are included in the assay medium depending on the nature of the assay to be conducted.

In some embodiments homogeneous immunoassays may be employed; such assays may also be referred to as essentially partition-free immunoassays. The present methods have application to fully automated homogeneous assays in which, prior to the assay, there is no extraction or separation of the analyte from other constituents of the sample including analyte metabolites. In a "non-manual extraction" assay, a sample such as a whole blood sample, without extraction in, e.g., an organic solvent, is combined with reagents for conducting an assay for the analyte in a suitable medium and the assay method is conducted. The present methods also find application to manual extraction assays. In either instance, a compound in accordance with the principles described herein may be employed to release the FKBP-binding immunosuppressant drug analyte from endogenous binding substances.

Homogeneous immunoassays are exemplified by the EMIT® assay (Syva Company, San Jose, Calif.) disclosed in Rubenstein, et al., U.S. Pat. No. 3,817,837, column 3, line 6 to column 6, line 64; immunofluorescence methods such as those disclosed in Ullman, et al., U.S. Pat. No. 3,996,345, column 17, line 59, to column 23, line 25; enzyme channeling immunoassays ("ECIA") such as those disclosed in Maggio, et al., U.S. Pat. No. 4,233,402, column 6, line 25 to column 9, line 63; and the fluorescence polarization immunoassay ("FPIA") as disclosed, for example, in, among others, U.S. Pat. No. 5,354,693.

Other enzyme immunoassays are the enzyme modulate mediated immunoassay ("EMMIA") discussed by Ngo and Lenhoff, FEBS Lett. (1980) 116:285-288; the substrate labeled fluorescence immunoassay ("SLFIA") disclosed by Oellerich, J. Clin. Chem. Clin. Biochem. (1984) 22:895-904; the combined enzyme donor immunoassays ("CEDIA") disclosed by Khanna, et al., Clin. Chem. Acta (1989) 185:231-240; homogeneous particle labeled immunoassays such as particle enhanced turbidimetric inhibition immunoassays ("PETINIA"), and particle enhanced turbidimetric immunoassay ("PETIA"), for example.

Other assays include the sol particle immunoassay ("SPIA"), the disperse dye immunoassay ("DIA"); the metalloimmunoassay ("MIA"); the enzyme membrane immunoassays ("EMIA"); luminoimmunoassays ("LIA"); and acridinium ester label immunoassays using paramagnetic particles as a solid phase (ADVIA Centaur immunoassays); for example. Other types of assays include immunosensor assays involving the monitoring of the changes in the optical, acoustic and electrical properties of an antibody-immobilized surface upon the binding of a hydrophobic drug. Such assays include, for example, optical immunosensor assays, acoustic immunosensor assays, semiconductor immunosensor assays, electrochemical transducer immunosensor assays, potentiometric immunosensor assays, and amperometric electrode assays.

In many of the assays discussed herein for determination of an analyte, a label is employed; the label is usually part of a signal producing system ("sps"). The nature of the label is dependent on the particular assay format. A signal producing system usually includes one or more components, at least one component being a detectable label, which generates a detectable signal that relates to the amount of bound and/or unbound label, i.e. the amount of label bound or not bound to the analyte being detected or to an agent that reflects the amount of the analyte to be detected. The label is any molecule that produces or can be induced to produce a signal, and may be, for example, a fluorescer, a radiolabel, an enzyme, a chemiluminescer or a photosensitizer. Thus, the signal is detected and/or measured by detecting enzyme activity, luminescence, light absorbance or radioactivity, depending on the nature of the label.

Suitable labels include, by way of illustration and not limitation, enzymes such as alkaline phosphatase, glucose-6-phosphate dehydrogenase ("G6PDH"), β-galatosidase, and horseradish peroxidase; ribozyme; a substrate for a replicase such as QB replicase; promoters; dyes; fluorescers, such as fluorescein, isothiocyanate, rhodamine compounds, phycoerythrin, phycocyanin, allophycocyanin, o-phthaldehyde, and fluorescamine; complexes such as those prepared from CdSe and ZnS present in semiconductor nanocrystals known as Quantum dots; chemiluminescers such as isoluminol and acridinium esters, for example; sensitizers; coenzymes; enzyme substrates; radiolabels such as $^{125}I$, $^{131}I$, $^{14}C$, $^{3}H$, $^{57}Co$ and $^{75}Se$; particles such as latex particles, carbon particles, metal particles including magnetic particles, e.g., chromium dioxide ($CrO_2$) particles, and the like; metal sol; crystallite; liposomes; cells, etc., which may be further labeled with a dye, catalyst or other detectable group. Suitable enzymes and coenzymes are disclosed in Litman, et al., U.S. Pat. No. 4,275,149, columns 19-28, and Boguslaski, et al., U.S. Pat. No. 4,318,980, columns 10-14; suitable fluorescers and chemiluminescers are disclosed in Litman, et al., U.S. Pat. No. 4,275,149, at columns 30 and 31; which are incorporated herein by reference.

The label can directly produce a signal and, therefore, additional components are not required to produce a signal. Numerous organic molecules, for example fluorescers, are able to absorb ultraviolet and visible light, where the light absorption transfers energy to these molecules and elevates them to an excited energy state. This absorbed energy is then dissipated by emission of light at a second wavelength. Other labels that directly produce a signal include radioactive isotopes and dyes.

Alternately, the label may need other components to produce a signal, and the signal producing system would then include all the components required to produce a measurable signal. Such other components may include substrates, coenzymes, enhancers, additional enzymes, substances that react with enzymic products, catalysts, activators, cofactors, inhibitors, scavengers, metal ions, and a specific binding substance required for binding of signal generating substances. A detailed discussion of suitable signal producing systems can be found in Ullman, et al., U.S. Pat. No. 5,185,243, columns 11-13, the disclosure of which is incorporated herein by reference.

The label or other sps members can be bound to a support. An analyte or analyte analog may be bound to a solid support in any manner known in the art, provided only that the binding does not substantially interfere with the ability of the analyte or the analog to bind with an antibody. In some embodiments, the analyte or analyte analog may be coated or covalently bound directly to the solid phase or may have layers of one or more carrier molecules such as poly(amino acids) including proteins such as serum albumins or immunoglobulins, or polysaccharides (carbohydrates) such as, for example, dextran or dextran derivatives. Linking groups may also be used to covalently couple the solid support and the analyte. Other methods of binding the analyte are also possible. For instance, a solid support may have a coating of a binder for a small molecule such as, for example, avidin, an antibody, etc., and a small molecule such as, but not limited to, biotin or a hapten, for example, can be bound to the analyte or vice versa. The binding of components to the surface of a support may be direct or indirect, covalent or non-covalent and can be accomplished by well-known techniques, commonly available in the literature. See, for example, "Immobilized Enzymes," Ichiro Chibata, Halsted Press, New York (1978) and Cautrecasas, *J. Biol. Chem.*, 245:3059 (1970).

The support may be comprised of an organic or inorganic, solid or fluid, water insoluble material, which may be transparent or partially transparent. The support can have any of a number of shapes, such as particle, including bead, film, membrane, tube, well, strip, rod, planar surfaces (such as, e.g., plate, and paper), and fiber, for example. Depending on the type of assay, the support may or may not be suspendable in the medium in which it is employed. Examples of suspendable supports are polymeric materials such as latex, lipid bilayers or liposomes, oil droplets, cells and hydrogels, and magnetic particles, for example. Other support compositions include polymers, such as nitrocellulose, cellulose acetate, poly(vinyl chloride), polyacrylamide, polyacrylate, polyethylene, polypropylene, poly(4-methylbutene), polystyrene, polymethacrylate, poly(ethylene terephthalate), nylon, and poly(vinyl butyrate), either used by themselves or in conjunction with other materials.

The support may be a particle. The particles should have an average diameter of at least about 0.02 microns and not more than about 100 microns. In some embodiments, the particles have an average diameter from about 0.05 microns to about 20 microns, or from about 0.3 microns to about 10 microns. The particle may be organic or inorganic, swellable or non-swellable, porous or non-porous, preferably of a density approximating water, generally from about 0.7 g/mL to about 1.5 g/mL, and composed of material that can be transparent, partially transparent, or opaque. The particles can be biological materials such as cells and microorganisms, e.g., erythrocytes, leukocytes, lymphocytes, hybridomas, *streptococcus*, *Staphylococcus aureus*, *E. coli*, or viruses. The particles can also be particles comprised of organic and inorganic polymers, liposomes, latex particles, magnetic or non-magnetic particles, phospholipid vesicles, chylomicrons, or lipoproteins, for example. In some embodiments, the particles are chromium dioxide (chrome) particles or latex particles.

The polymer particles can be formed of addition or condensation polymers.

The particles will be readily dispersible in an aqueous medium and can be adsorptive or functionalizable so as to permit conjugation to an analyte, either directly or indirectly through a linking group. The particles can also be derived from naturally occurring materials, naturally occurring materials that are synthetically modified, and synthetic materials. Among organic polymers of particular interest are polysaccharides, particularly cross-linked polysaccharides, such a agarose, which is available as SEPHAROSE®, dextran, available as SEPHADEX® and SEPHACRYL®, cellulose, starch, and the like; addition polymers, such as polystyrene, polyvinyl alcohol, homopolymers and copolymers of derivatives of acrylate and methacrylate, particularly esters and amides having free hydroxyl functionalities, for example.

The label and/or other sps member may be bound to an sbp member or another molecule. For example, the label can be bound covalently to an sbp member such as, for example, an antibody, a receptor for an antibody, a receptor that is capable of binding to a small molecule conjugated to an antibody, or an analyte analog. Bonding of the label to the sbp member may be accomplished by chemical reactions that result in replacing a hydrogen atom of the label with a bond to the sbp member or may include a linking group between the label and the sbp member. Other sps members may also be bound covalently to sbp members. For example, two sps members such as a fluorescer and quencher can each be bound to a different antibody that forms a specific complex with the analyte. Formation of the complex brings the fluorescer and quencher in close proximity, thus permitting the quencher to interact with the fluorescer to produce a signal. Methods of conjugation are well known in the art. See, for example, Rubenstein, et al., U.S. Pat. No. 3,817,837, the relevant portions of which are incorporated herein by reference.

Enzymes of particular interest as label proteins are redox enzymes, particularly dehydrogenases such as glucose-6-phosphate dehydrogenase, and lactate dehydrogenase, for example, and enzymes that involve the production of hydrogen peroxide and the use of the hydrogen peroxide to oxidize a dye precursor to a dye. Particular combinations include saccharide oxidases, e.g., glucose and galactose oxidase, or heterocyclic oxidases, such as uricase and xanthine oxidase, coupled with an enzyme which employs the hydrogen peroxide to oxidize a dye precursor, that is, a peroxidase such as horse radish peroxidase, lactoperoxidase, or microperoxidase. Additional enzyme combinations are known in the art.

When a single enzyme is used as a label, other enzymes may find use such as hydrolases, transferases, and oxidoreductases, preferably hydrolases such as alkaline phosphatase and beta-galactosidase. Alternatively, luciferases may be used such as firefly luciferase and bacterial luciferase.

Illustrative co-enzymes that find use include, by way of illustration and not limitation, NAD[H], NADP[H], pyridoxal phosphate, FAD[H], FMN[H], and β-galactosidase, for example. See, for example, U.S. Pat. No. 4,318,980, the relevant portions of the disclosure of which are incorporated herein by reference.

With label proteins such as, for example, enzymes, the molecular weight range will be from about 10,000 to about 600,000, or from about 10,000 to about 300,000 molecular weight. There is usually at least about 1 analyte analog per about 200,000 molecular weight, or at least about 1 per about 150,000 molecular weight, or at least about 1 per about 100,000 molecular weight, or at least about 1 per about 50,000 molecular weight, for example. In the case of enzymes, the number of analyte analog groups is from 1 to about 20, about 2 to about 15, about 3 to about 12, or about 6 to about 10, for example.

The term "non-poly(amino acid) labels" includes those labels that are not proteins (e.g., enzymes). The non-poly(amino acid) label is capable of being detected directly or is detectable through a specific binding reaction that produces a detectable signal. The non-poly(amino acid) labels include, for example, radioisotopes, luminescent compounds, supports, e.g., particles, plates, beads, etc., polynucleotides, and the like. More particularly, the non-poly(amino acid) label can be isotopic or non-isotopic, usually non-isotopic, and can be a polynucleotide coding for a catalyst, promoter, dye, coenzyme, enzyme substrate, radioactive group, a small organic molecule (including, e.g., biotin, fluorescent molecules, chemiluminescent molecules, and the like), amplifiable polynucleotide sequence, a support such as, for example, a particle such as latex or carbon particle or chromium dioxide (chrome) particle, a metal sol, a crystallite, a liposome, or a cell, which may or may not be further labeled with a dye, catalyst or other detectable group, for example.

In one embodiment the assay is an induced luminescence immunoassay, which is described in U.S. Pat. No. 5,340,716 (Ullman, et al.) entitled "Assay Method Utilizing Photoactivated Chemiluminescent Label" ("induced luminescence assay"), which disclosure is incorporated herein by reference. In one approach the assay uses a particle incorporating a photosensitizer and a label particle incorporating a chemiluminescent compound. The label particle is conjugated to an sbp member, for example, an antibody for the analyte that is capable of binding to the analyte to form a complex, or to a second sbp member to form a complex, in relation to the amount of the analyte. If the analyte is present, the photosensitizer and the chemiluminescent compound come into close proximity. The photosensitizer generates singlet oxygen and activates the chemiluminescent compound when the two labels are in close proximity. The activated chemiluminescent compound subsequently produces light. The amount of light produced is related to the amount of the complex formed, which comprises antibody for the analyte.

By way of further illustration and not limitation, chemiluminescent particles are employed, which comprise the chemiluminescent compound associated therewith such as by incorporation therein or attachment thereto. An sbp member that binds to the analyte, such as, for example, an antibody for analyte, is bound to a polysaccharide coating the particles. A second sbp member that binds to the antibody for the analyte is part of a biotin conjugate. Streptavidin is conjugated to a second set of particles having a photosensitizer associated therewith. The binding of the streptavidin to this second set of particles (photosensitizer particles) may or may not involve a polysaccharide on the particles. The chemiluminescent particles are mixed with the sample suspected of containing an analyte and with the photosensitizer particles. The reaction medium is incubated to allow the particles to bind to the analyte by virtue of the binding of the sbp member to the analyte to form a complex and to allow the second sbp member to bind to the complex. Then, the medium is irradiated with light to excite the photosensitizer, which is capable in its excited state of activating oxygen to a singlet state. Because the chemiluminescent compound of one of the sets of particles is now in close proximity to the photosensitizer by virtue of the presence of the analyte, it is activated by singlet oxygen and emits luminescence. The medium is then examined for the amount of luminescence or light emitted, the presence thereof being related to the amount of the analyte.

Another particular example of an assay that may be employed for the determination of an analyte is discussed in U.S. Pat. No. 5,616,719 (Davalian, et al.), which describes fluorescent oxygen channeling immunoassays.

The assays discussed above are normally carried out in an aqueous buffered medium at a moderate pH, generally that which provides optimum assay sensitivity. The pH for the assay medium will usually be in the range of about 4 to about 11, or in the range of about 5 to about 10, or in the range of about 6.5 to about 9.5. The pH will usually be a compromise between optimum binding of the binding members of any specific binding pairs, and the pH optimum for other reagents of the assay such as members of a signal producing system, for example. Various buffers may be used to achieve the desired pH and maintain the pH during the incubation period.

Illustrative buffers include, but are not limited to, borate, phosphate, carbonate, Tris, barbital, PIPES, HEPES, MES, ACES, MOPS, and BICINE, for example. Various ancillary materials may be employed in the assay methods. For example, in addition to buffers and preservatives, the medium may comprise stabilizers for the medium and for the reagents employed. In some embodiments, in addition to these additives, proteins may be included, such as albumins; quaternary ammonium salts; polyanions such as dextran sulfate; and binding enhancers, for example. All of the above materials are present in a concentration or amount sufficient to achieve the desired effect or function.

One or more incubation periods may be applied to the medium at one or more intervals including any intervals between additions of various reagents mentioned above. The medium is usually incubated at a temperature and for a time sufficient for binding of various components of the reagents to occur. Moderate temperatures are normally employed for carrying out the method and usually constant temperature, preferably, room temperature, during the period of the measurement. Incubation temperatures normally range from about 5° C. to about 99° C., or from about 15° C. to about 70° C., or about 20° C. to about 45° C., for example. The time period for the incubation is about 0.2 seconds to about 24 hours, or about 1 second to about 6 hours, or about 2 seconds to about 1 hour, or about 1 to about 15 minutes, for example. The time period depends on the temperature of the medium and the rate of binding of the various reagents. Temperatures during measurements will generally range from about 10° C. to about 50° C., or from about 15° C. to about 40° C.

The concentration of analyte that may be assayed generally varies from about $10^{-5}$ to about $10^{-17}$ M, or from about $10^{-6}$ to about $10^{-14}$ M. Considerations, such as whether the assay is qualitative, semi-quantitative or quantitative (relative to the amount of erythrocytophilic drug analyte present in the sample), the particular detection technique and the concentration of the analyte normally determine the concentrations of the various reagents.

The concentrations of the various reagents in the assay medium will generally be determined by the concentration range of interest of the analyte, the nature of the assay, the antibody affinity and avidity and antibody fragmentation, for example. However, the final concentration of each of the reagents is normally determined empirically to optimize the sensitivity of the assay over the range. That is, a variation in concentration of analyte that is of significance should provide an accurately measurable signal difference. Considerations such as the nature of a signal producing system and the nature of the analyte normally determine the concentrations of the various reagents.

While the order of addition may be varied widely, there will be certain preferences depending on the nature of the assay. The simplest order of addition is to add all the materials simultaneously and determine the effect that the assay medium has on the signal as in a homogeneous assay. Alternatively, the reagents can be combined sequentially. Optionally, an incubation step may be involved subsequent to each addition as discussed above. The length of the incubation period is that which is sufficient to accomplish the desired function.

Specific Embodiments of Assays for FKBP-Binding Immunosuppressant Drug Analytes

Specific embodiments of assays that may be employed to assay the sample are discussed next by way of illustration and not limitation. In all instances a compound in accordance with the principles described herein is added to the sample, either prior to and separate from conducting an assay or concomitantly with conducting an assay, to release the FKBP-binding immunosuppressant drug from endogenous binding substances. The compound may be included in a medium comprising a sample or the sample may be added to a separately prepared pretreatment reagent solution comprising the compound in accordance with the principles described herein.

In a homogeneous assay, after all of the reagents have been combined, the signal is determined and related to the amount of analyte in the sample. For example, in an EMIT® assay for an analyte, a sample suspected of containing the analyte is combined in an aqueous medium either simultaneously or sequentially with an enzyme conjugate of the analyte, i.e., an analog of the analyte, and antibody capable of recognizing the analyte. Generally, a substrate for the enzyme is added, which results in the formation of a chromogenic or fluorogenic product upon enzyme catalyzed reaction. Preferred enzymes are glucose-6-phosphate dehydrogenase and alkaline phosphatase but other enzymes may be employed. The analyte and the moieties of the enzyme conjugate compete for binding sites on the antibody. The enzyme activity in the medium is then measured, usually by spectrophotometric means.

An "analyte analog" or "analog of the analyte" is a modified analyte that competes with the analyte for a receptor such as an antibody for the analyte. The modification may provide means to join an analyte analog to another molecule such as, but not limited to, a support, a label, a small molecule, or a binding partner for a small molecule, for example. The analyte analog will usually differ from the analyte by more than replacement of a hydrogen with a bond which links the analyte analog to a hub or label, but need not. That is, the analyte analog may be linked to another molecule directly or indirectly by means of a linking group. The analyte analog may be, for example, a molecule structurally related to the analyte or the analyte conjugated to another molecule through a linking group.

The aforementioned assays may be carried out using mutant glucose-6-phosphate dehydrogenase as the enzyme of the enzyme conjugate. This mutant enzyme is described in U.S. Pat. Nos. 6,090,567 and 6,033,890, the relevant disclosures of which are incorporated herein by reference. Furthermore, the assay may be conducted using antibodies for the analyte and using procedures as disclosed in U.S. Pat. Nos. 5,328,828 and 5,135,863, the relevant disclosures of which are incorporated herein by reference.

Heterogeneous assays usually involve one or more separation steps and can be competitive or non-competitive. A variety of competitive and non-competitive assay formats are disclosed in Davalian, et al., U.S. Pat. No. 5,089,390, column 14, line 25 to column 15, line 9, which disclosure is incorporated herein by reference. In one type of competitive assay, a support, as discussed herein, having antibodies for the analyte bound thereto is contacted with a medium containing the sample and appropriate enzyme conjugates of the analyte. After separating the support and the medium, the enzyme activity of the support or the medium is determined by conventional techniques to determine the measurement result.

In certain embodiments a second enzyme may be employed in addition to the enzyme of the enzyme conjugate. The enzymes of the pair of enzymes are related in that a product of the first enzyme serves as a substrate for the second enzyme.

Another embodiment of an assay format is a capture assay. In this assay format, the antibody for the analyte is covalently bound to a magnetic particle. The sample is incubated with these particles to allow the antibodies for the analyte to bind to the analyte. Subsequently, an enzyme that has the analyte or a derivative of the analyte covalently attached is incubated with the magnetic particles. After washing, the amount of enzyme that is bound to the magnetic particles is measured and is inversely related to the amount of a complex comprising the antibody for the analyte.

In a particular example, an induced luminescence immunoassay may be employed. The induced luminescence immunoassay is referred to in U.S. Pat. No. 5,340,716 (Ullman), which disclosure is incorporated herein by reference. In one approach, the assay uses a particle having associated therewith a photosensitizer where an analog of the FKBP-binding immunosuppressant drug is bound to the particle (photosensitizer particle reagent). The chemiluminescent reagent comprises an antibody for the FKBP-binding immunosuppressant drug. The FKBP-binding immunosuppressant drug analyte competes with the photosensitizer particle reagent for binding to the antibody for FKBP-binding immunosuppressant drug. If the FKBP-binding immunosuppressant drug analyte is present, the fewer is the number of molecules of photosensitizer particle reagent that come into close proximity with the chemiluminescent reagent. Therefore, there will be a decrease in the assay signal. The photosensitizer generates singlet oxygen and activates the chemiluminescent reagent when the two labels are in close proximity. The activated chemiluminescent reagent subsequently produces light. The amount of light produced is related to the amount of the complex formed, which in turn is related to the amount of FKBP-binding immunosuppressant drug analyte present in the sample.

In another particular example of an induced luminescence immunoassay, the assay uses a particle having associated therewith a chemiluminescent compound where an analog of the FKBP-binding immunosuppressant drug analyte is bound to the particle (chemiluminescent particle reagent). The photosensitizer reagent comprises an antibody for FKBP-binding immunosuppressant drug. The FKBP-binding immunosuppressant drug analyte competes with the chemiluminescent particle reagent for binding to the antibody for FKBP-binding immunosuppressant drug. If the FKBP-binding immunosuppressant drug analyte is present, the fewer is the number of molecules of chemiluminescent particle reagent that come into close proximity with the photosensitizer reagent. Therefore, there will be a decrease in the assay signal. The photosensitizer generates singlet oxygen and activates the chemiluminescent compound of the chemiluminescent particle reagent when the two labels are in close proximity. The activated chemiluminescent compound subsequently produces light. The amount of light produced is related to the amount of the complex formed, which in turn is related to the amount of FKBP-binding immunosuppressant drug analyte present in the sample.

In another particular example of an induced luminescence assay, a photosensitizer particle is employed that is conjugated to a binding partner for a small molecule such as, for example, avidin or streptavidin (which are binding partners for biotin). An analog of the FKBP-binding immunosuppressant drug that comprises biotin (biotin reagent) is also employed. A chemiluminescent reagent that comprises a specific binding member for the FKBP-binding immunosuppressant drug is employed as part of the detection system. The reaction medium is incubated to allow the avidin or streptavidin of the photosensitizer particles to bind to the biotin reagent by virtue of the binding between avidin and biotin and to also allow the specific binding member for the FKBP-binding immunosuppressant drug that is part of the chemiluminescent reagent to bind to the FKBP-binding immunosuppressant drug analyte or to the analyte analog of the biotin reagent that is now attached to the photosensitizer particles.

Then, the medium is irradiated with light to excite the photosensitizer, which is capable in its excited state of activating oxygen to a singlet state. Because less of the chemiluminescent reagent is now in close proximity to the photosensitizer because of the presence of the FKBP-binding immunosuppressant drug analyte, there is less activation of the chemiluminescent reagent by the singlet oxygen and less luminescence. The medium is then examined for the presence and/or the amount of luminescence or light emitted, the presence thereof being related to the presence and/or amount of the FKBP-binding immunosuppressant drug analyte where a decrease in signal is observed in the presence of the FKBP-binding immunosuppressant drug analyte.

In another particular example of an induced luminescence assay, a photosensitizer particle is employed that is conjugated to a binding partner for a small molecule such as, for example, avidin or streptavidin (which are binding partners for biotin). A conjugate reagent comprises a specific binding member for FKBP-binding immunosuppressant drug conjugated to biotin. An analog of the FKBP-binding immunosuppressant drug is employed where the analog is attached to a chemiluminescent particle (chemiluminescent-analog reagent) is also employed. The reaction medium is incubated to allow the avidin or streptavidin of the photosensitizer particles to bind to the antibody-biotin reagent by virtue of the binding between avidin and biotin and to also allow the specific binding member for the FKBP-binding immunosuppressant drug to bind to FKBP-binding immunosuppressant drug analyte if present in the sample and to the analyte analog that is part of the chemiluminescent-compound reagent. Then, the medium is irradiated with light to excite the photosensitizer, which is capable in its excited state of activating oxygen to a singlet state. Because less of the chemiluminescent-analog reagent is now in close proximity to the photosensitizer because of the presence of the FKBP-binding immunosuppressant drug analyte, there is less activation of the chemiluminescent reagent by the singlet oxygen and less luminescence. The medium is then examined for the presence and/or the amount of luminescence or light emitted, the presence thereof being related to the presence and/or amount of the FKBP-binding immunosuppressant drug analyte where a decrease in signal is observed in the presence of the FKBP-binding immunosuppressant drug analyte.

Another example, by way of illustration and not limitation, of an assay format is ACMIA (Affinity Chromium dioxide Mediated Immuno Assay). For the ACMIA assay format, chrome particles, which are coated with an analog of the FKBP-binding immunosuppressant drug, are employed as a first component. A second component is an antibody for the FKBP-binding immunosuppressant drug. This antibody, crosslinked to a reporter enzyme (for example, β-galactosidase), is added to a reaction vessel in an excess amount, i.e., an amount greater than that required to bind all of the FKBP-binding immunosuppressant drug analyte that might be present in a sample. A sample that is subjected to treatment with a releasing agent in accordance with the principles described herein is treated with an antibody for the FKBP-binding immunosuppressant drug, which antibody binds to the FKBP-binding immunosuppressant drug in the sample. The antibody-enzyme conjugate is mixed with sample to allow the FKBP-binding immunosuppressant drug analyte to bind to the antibody. Next, the chrome particle reagent is added to bind up any excess antibody-enzyme conjugate. Then, a magnet is applied, which pulls all of the chrome particles and excess antibody-enzyme out of the suspension, and the supernatant is transferred to a final reaction container. The substrate of the reporter enzyme is added to the final reaction container, and the enzyme activity is measured spectrophotometrically as a change in absorbance over time. The amount of this signal is related to the amount of the FKBP-binding immunosuppressant drug in the sample.

In all of the above assay formats, a releasing agent in accordance with the principles described herein is employed to displace the FKBP-binding immunosuppressant drug from endogenous binding substances. As discussed above, the releasing agent may be added to a medium comprising the sample either directly or in the form of a pretreatment reagent solution. On the other hand, the sample may be added to a pretreatment reagent solution comprising a compound in accordance with the principles described herein.

Measurement Step

Methods in accordance with the principles described herein wherein an immunoassay is used comprise examining each respective assay medium for the amount of a complex comprising the antibody for the FKBP-binding immunosuppressant drug analyte (anti-analyte antibody). The measurement is carried out respectively for each assay medium following the incubation of the assay medium in accordance with the particular assay employed.

The phrase "measuring the amount of an analyte" refers to the quantitative, semi-quantitative and qualitative determination of the analyte. Methods that are quantitative, semi-quantitative and qualitative, as well as all other methods for determining the analyte, are considered to be methods of measuring the amount of the analyte. For example, a method, which merely detects the presence or absence of the analyte in a sample suspected of containing the analyte, is considered to be included within the scope of the present embodiments. The terms "detecting" and "determining," as well as other common synonyms for measuring, are contemplated within the scope of the present embodiments.

In many embodiments the examination of the medium involves detection of a signal from the medium. The amount of the signal is related to the amount of the analyte in the sample. The particular mode of detection depends on the nature of the signal producing system. As discussed herein, there are numerous methods by which a label of an sps can produce a signal detectable by external means, desirably by visual examination, and include, for example, electromagnetic radiation, electrochemistry, heat, radioactivity detection, and chemical reagents.

Activation of a signal producing system depends on the nature of the signal producing system members. For those members of a signal producing system that are activated with light, the member is irradiated with light. For members of signal producing systems that are on the surface of a particle, addition of a base may result in activation. Other activation methods will be suggested to those skilled in the art in view of the disclosures herein. For some signal producing systems, no agent for activation is necessary such as those systems that involve a label that is a radioactive label, an enzyme, and so forth. For enzyme systems, addition of a substrate and/or a cofactor may be necessary.

The examination for amount of the signal also includes the detection of the signal, which is generally merely a step in which the signal is read. The signal is normally read using an instrument, the nature of which depends on the nature of the signal. The instrument may be a spectrophotometer, fluorometer, absorption spectrometer, luminometer, chemiluminometer, actinometer, or a photographic instrument, for example. The amount of signal detected is related to the amount of the FKBP-binding immunosuppressant drug analyte present in a sample. Temperatures during measurements generally range from about 10° C. to about 70° C., or from about 20° C. to about 45° C., or about 20° C. to about 25° C., for example. In one approach standard curves are formed using known concentrations of the analytes to be screened; calibrators and other controls may also be used.

Kits for Conducting Assays on the Sample Portions

The reagents for conducting a particular assay may be present in a kit useful for conveniently performing an assay for the determination of an FKBP-binding immunosuppressant drug analyte. In one embodiment a kit comprises in packaged combination a reagent in accordance with the principles described herein for releasing the FKBP-binding immunosuppressant drug analyte from endogenous binding substances, an antibody for the analyte and other reagents for performing an assay, the nature of which depend upon the particular assay format. The reagents may each be in separate containers or various reagents can be combined in one or more containers depending on the cross-reactivity and stability of the reagents. The kit can further include other separately packaged reagents for conducting an assay such as additional sbp members, ancillary reagents such as an ancillary enzyme substrate, and so forth.

The relative amounts of the various reagents in the kits can be varied widely to provide for concentrations of the reagents that substantially optimize the reactions that need to occur during the assay method and further to optimize substantially the sensitivity of the assay. Under appropriate circumstances one or more of the reagents in the kit can be provided as a dry powder, usually lyophilized, including excipients, which on dissolution will provide for a reagent solution having the appropriate concentrations for performing a method or assay. The kit can further include a written description of a method in accordance with the present embodiments as described above.

The phrase "at least" as used herein means that the number of specified items may be equal to or greater than the number recited. The phrase "or more" as used herein means that the number of specified items may be equal to or greater than the number recited. The phrase "about" as used herein means that the number recited may differ by plus or minus 10%; for example, "about 5" means a range of 4.5 to 5.5.

The following discussion is directed to specific examples in accordance with the principles described herein by way of illustration and not limitation; the specific examples are not intended to limit the scope of the present disclosure and the appended claims. Numerous modifications and alternative compositions, methods, and systems may be devised without departing from the spirit and scope of the present disclosure.

EXAMPLES

The following examples further describe the specific embodiments of the invention by way of illustration and not limitation and are intended to describe and not to limit the scope of the invention. Parts and percentages disclosed herein are by volume unless otherwise indicated.

DEFINITIONS mg=milligram
g=gram(s)
ng=nanogram(s)
mL=milliliter(s)
µL=microliter(s)
mmol(s)=millimole(s)
µmol=micromolar
° C.=degrees Centigrade
min=minute(s)

sec=second(s)
hr=hour(s)
w/v=weight to volume
v/v=volume to volume
TLC=thin layer chromatography
HPLC=high performance liquid chromatography
EtOAc=ethyl acetate
MeOH=methanol
DMF=dimethylformamide
DMSO=dimethylsulfoxide
MeOP=1-methoxy-2-propanol
MES=2-(N-morpholino)ethanesulfonic acid
DI=deionized
EDA=ethylene diamine
LOCI=luminescent oxygen channeling immunoassay
BSA=bovine serum albumin
BGG=bovine gamma globulin
mIgG=monoclonal immunoglobulin
MS=mass spectrometry
SIRO=sirolimus
Tacro=tacrolimus
FKE=FK506 ester All chemicals may be purchased from the Sigma-Aldrich Company (St. Louis Mo.) unless otherwise noted. Tacrolimus may be obtained from Astellas Pharma US. Inc., Deerfield Ill. Sirolimus may be obtained from Pfizer Inc., New York N.Y. 4-phenyl-1,2,4-triazoline-3,5-dione (PTAD) may be obtained from Sigma-Aldrich Company. diethyl azidodicarboxylate (DAC) may be obtained from Sigma-Aldrich Company.

Testing was carried out using the DIMENSION® RxL analyzer, available from Siemens Healthcare Diagnostics Inc., Newark Del. The instrument was employed using ACMIA immunoassay technology. The ACMIA assay method is described in U.S. Pat. Nos. 7,842,475, 7,186,518, 5,147,529, 5,128,103, 5,158,871, 4,661,408, 5,151,348, 5,302,532, 5,422,284, 5,447,870, and 5,434,051, the disclosures of which are incorporated herein in their entirety. In the embodiment of the ACMIA method used herein and discussed in more detail below, competition between tacrolimus analog on chrome particles and tacrolimus in patient samples for antibody for tacrolimus conjugated to an enzyme (the "conjugate") is utilized to determine the amount of tacrolimus in patient samples. Conjugate that binds to the tacrolimus analog on chrome particles is removed by magnetic separation. The enzymatic activity from the conjugate remaining in the supernatant is measured and is directly proportional to the amount of tacrolimus in the patient sample. In the ACMIA assay format employed, the enzymatic activity observed when testing a sample containing no tacrolimus is indicative of the amount of enzymatic activity that is not bound to active antibody (i.e., cannot bind tacrolimus on chrome particles). The enzymatic activity observed when no chrome particle is present is indicative of the total amount of enzymatic activity in the conjugate. These values can be used to estimate the percent of enzymatic activity bound to active antibody.

Example 1

Preparation of Diels-Alder adducts of 4-phenyl-1,2,4-triazoline-3,5-dione (PTAD) and sirolimus. Reference is made to FIG. 5. A solution of PTAD (38 mg, 0.217 mmols) in anhydrous $CH_2Cl_2$ (1 ml) was added to a solution of sirolimus (200 mg, 0.219 mmols) in anhydrous $CH_2Cl_2$ (7 ml) at room temperature (24° C.). The characteristic red color of PTAD disappeared. The reaction mixture was stirred at room temperature for 30 minutes and refluxed under nitrogen at 60° C. for 60 min. TLC analysis of the mixture showed that very small amount of sirolimus remained. (TLC conditions: Hexane/ethyl acetate/MeOH=30/65/5 (v/v)). Then, 5 mg of PTAD was added to the reaction mixture. The mixture was stirred at 24° C. for 30 min. TLC analysis of the mixture again demonstrated that all sirolimus was consumed. The light red color of PTAD remained in the reaction indicating an excess of PTAD. Most of the $CH_2Cl_2$ was evaporated by rotary evaporation. The residue solution (0.5 ml) was applied to a preparative TLC plate (20×20 cm, 2000 micron; Analtech, Newark Del.). The plate was developed with the same solvent system as above (Hexane/ethyl acetate/MeOH=30/65/5 (v/v)). The silicon band containing product was collected and extracted with MeOH/$CH_2Cl_2$ (1/9; v/v; 40 ml×3) three times. The combined organic extracts were evaporated and the residue was dried in high vacuum for 16 hr. This gave a mixture of the desired pure PTAD-sirolimus Diels-Alder adducts III and IV (220 mg, 92% yield) as a white solid. HPLC region-isomers ratio of III/IV was 86/14; HPLC-MS (ES): MNa$^+$ 1111.5; $^1$H-NMR (CDCl$_3$) 7.62 (1H); 7.46 (3H); 7.37 (1H); 5.98 (1H); 5.84 (1H); 5.55 (1H); 3.4 (s, 3H); 3.35 (s, 3H); 3.15 (s, 3H); 0.72 (q, 1H).

Figure 6:
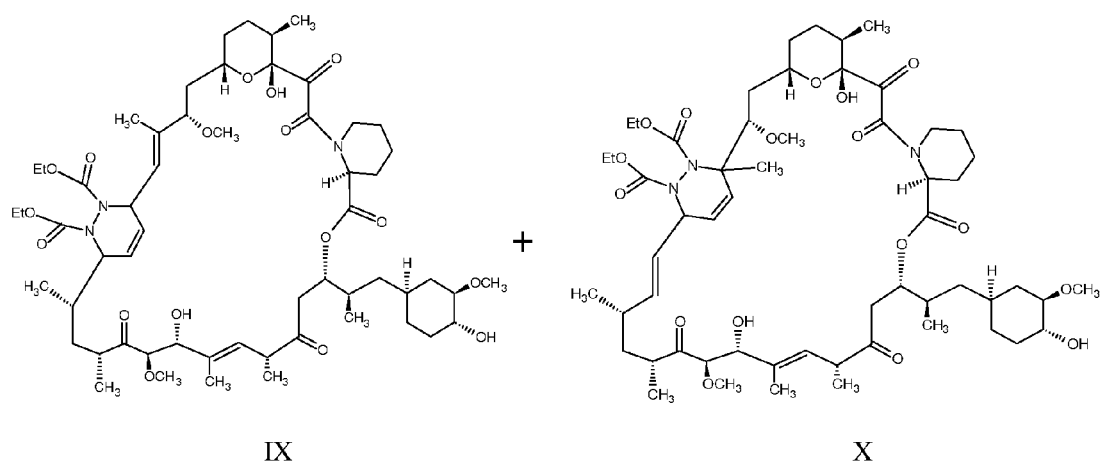
FIG. 6 depicts compounds not in accordance with the principles described herein but provided for purposes of comparison.

Preparation of Diels-Alder adducts of diethyl azidodicarboxylate (DAC) and sirolimus. The title compound, which is not in accordance with the principles described herein, was prepared and evaluated for purposes of comparison. DAC (77 mg, 0.07 ml, 0.438 mmol) was added to a solution of sirolimus (200 mg, 0.219 mmol) in anhydrous $CH_2Cl_2$ (5 ml) at room temperature (24° C.). The reaction mixture was stirred at room temperature for 10 min and refluxed under nitrogen at 60° C. for 16 hr. TLC analysis of the mixture showed that small amount of sirolimus remains (TLC condition: ethyl acetate). Thus, the mixture was allowed to cool to room temperature (24° C.). DAC (77 mg) was added to the reaction mixture. The reaction mixture was refluxed under nitrogen at 60° C. for 3 hr. Most of the $CH_2Cl_2$ was evaporated by rotary evaporation. The residue solution (0.5 ml) was applied to a preparative TLC plate (20×20 cm, 2000 micron; Analtech). The plate was developed with the same solvent system (ethyl acetate). The silicon band containing product was collected and extracted with MeOH/$CH_2Cl_2$ (119; v/v; 40 ml×3) three times. The combined organic extracts were evaporated and the residue was dried in high vacuum for 16 hr. This gave the desired pure sirolimus Diels-Alder adducts IX and X (see FIG. 6) (182 mg, 76% yield) as a white solid. HPLC region-isomers IX/X ratio was 85/15; HPLC-MS (ES): MNa+ 1110.6.

Figure 7:
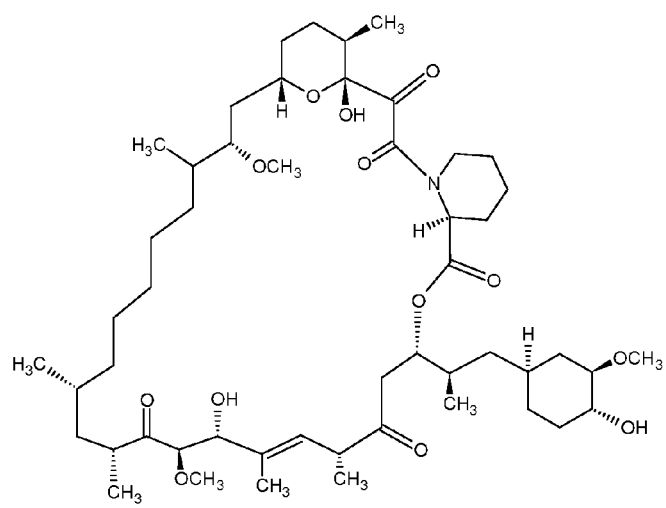
FIG. 7 depicts a compound not in accordance with the principles described herein but provided for purposes of comparison.

Preparation of hydrogenated sirolimus. The title compound, which is not in accordance with the principles described herein, was prepared and evaluated for purposes of comparison. Hydrogenated sirolimus was prepared in a manner similar to that described in U.S. Pat. No. 5,023,262, the relevant portions of which are incorporated herein by reference. In summary, the hydrogenation of sirolimus was conducted with a metal catalyst under hydrogen pressure to hydrogenate the triene portion of sirolimus to give hydrogenated sirolimus XI (see FIG. 7).

Preparation of pretreatment reagent solution. This pretreatment solution was prepared to contain an amount of releasing agent, 6.8 mg/mL PIPES 1.5 sodium salt (buffer), 0.3 mg/mL EDTA disodium (clot prevention agent), 1.0 mg/mL saponin (hemolytic agent), 0.2% PROCLIN® 300 (preservative), 0.024 mg/mL neomycin sulfate (preservative) and 0.99 mg/mL NaN$_3$, pH 6.5. The amount of releasing agent in each of the pretreatment reagent solutions was 10 µg/mL. The releasing agent concentration in the final reaction mixture was equivalent to 46.7 µg/mL of the analog added from the sample.

Preparation of anti-sirolimus antibody-β-galactosidase conjugate. Monoclonal anti-sirolimus antibody (clone 155-M1 from Wyeth Pharmaceutical) was conjugated to β-galactosidase using a standard heterobifunctional SMCC (succinimidyl trans-4-(N-maleimidylmethyl)cyclohexane-1-carboxylate) linker according to known techniques. The antibody conjugate solution contained approximately 7.5 µg/mL anti-sirolimus antibody-β-galactosidase conjugate, 30 mg/mL protease free bovine serum albumin, 0.126 mg/mL $MgCl_2$, 0.03 mL/mL of ethylene glycol, 35.14 mg/mL PIPES 1.5 sodium salt, 50 mg/mL NaCl and beta-gal mutein (inactivated β-galactosidase), pH 6.5.

Preparation of anti-tacrolimus antibody-β-galactosidase conjugate. Monoclonal anti-tacrolimus antibody (clone 1H6, see for example U.S. Pat. No. 7,078,495) is conjugated to β-galactosidase using a standard heterobifunctional SMCC (succinimidyl trans-4-(N-maleimidylmethyl)cyclohexane-1-carboxylate) linker according to known techniques. The antibody conjugate solution contains approximately 7.5 µg/mL anti-tacrolimus antibody-β-galactosidase conjugate, 30 mg/mL protease free bovine serum albumin, 0.126 mg/mL $MgCl_2$, 0.03 mL/mL of ethylene glycol, 35.14 mg/mL PIPES 1.5 sodium salt, 50 mg/mL NaCl and beta-gal mutein (inactivated β-galactosidase), pH 6.5.

Magnetic chrome particle preparation. Sirolimus chrome particles (immunoassay solid phase) were prepared by conjugating sirolimus-biotin conjugate to streptavidin-coated chrome particle (prepared in a manner similar to that described in U.S. Pat. No. 7,842,475). The chrome particle reagent contained approximately 2.5 mg/mL sirolimus chrome particle slurry, 60.8 mg/mL trehalose dihydrate and 7.2 mg/mL CARBOWAX®.

Tacrolimus chrome particles (immunoassay solid phase) were prepared by conjugating tacrolimus-C22 succinate (prepared in a manner similar to that described in U.S. Pat. No. 7,842,475) to fluorescein, which was used to pre-decorate anti-fluorescein antibody immobilized on chromium dioxide particles through glutaraldehyde. The chrome particle reagent contained approximately 2.5 mg/mL tacrolimus chrome particle slurry, 60.8 mg/mL trehalose dihydrate and 7.2 mg/mL CARBOWAX®.

Preparation of samples. Aliquots of a whole blood pool are spiked with an amount of sirolimus so that the resulting concentration of sirolimus in the whole blood samples in the calibrators is as set forth in Table 1 (0.0, 5.1, 10.1, 20.6 and 31.6 ng/mL). Aliquots of a whole blood pool are spiked with an amount of tacrolimus so that the resulting concentration of sirolimus in the whole blood samples in the calibrators is as set forth in Table 2 (0.0, 2.6, 5.3, 11.6 and 30.1 ng/mL).

Pretreatment of samples. A set of samples was treated as follows: To each sample was added an amount of the pretreatment reagent solution from above for displacing sirolimus in the sample from endogenous specific binding proteins. The samples were incubated at 37° C. for a period of 140 minutes. Subsequently, each sample was subjected to the aforementioned assay, which is further described below; and signal (mAU) was measured and related to a concentration of analyte that represents the amount of free analyte (analyte that is not bound by endogeneous binding substances plus analyte that was displaced from endogeneous binding substances) in the samples.

Assay. The ACMIA assay for sirolimus was carried out as follows: 15 µL of a whole blood sample from above was mixed with the pretreatment reagent solution from above (Displacer) (Table 1) in a vessel on the DIMENSION® RxL analyzer. The whole blood was sampled from a standard cup by first mixing the blood with the ultrasonic sample probe.

Anti-sirolimus antibody-β-galactosidase conjugate (50 µL) was added next to each of the reaction vessels and the mixture was held for a period of time (10 to 15 minutes) and at a temperature of 43° C. to allow sirolimus, if present, to react with the antibody reagent. Chrome particles with immobilized sirolimus-biotin conjugate to streptavidin-coated chrome particle were added (50 µL) to each of the reaction vessels and were allowed to bind un-bound conjugate. The sirolimus-bound anti-sirolimus antibody-β-galactosidase conjugate does not bind to the chrome particles but remains in the supernatant when a magnetic field is applied to the above reaction mixtures to separate the solution from the chrome particles. The sirolimus-bound conjugate was detected by transferring the supernatant from each of the reaction vessels to a photometric cuvette and measuring the enzymatic rate of the conjugate in the presence of chlorophenol red-β-D-galactopyranoside (CPRG). The rate for each reaction vessel was measured bichromatically at 577 and 700 nm. The results are summarized in Table 1 under the categories: instrument signal observed for calibrators, drug concentration measured in ng/mL, percent (%) displaced vs. SIRO and calculated antibody cross-reactivity (percent (%) times 100). Cross-reactivity was based on the following:

1) 70 µL of pretreatment reagent solution was added to the reaction medium versus 15 µL of sample, total reaction mixture volume=305 µL.
2) 10 µg/mL of SIRO analog was in the pretreatment reagent solution.
3) 10 µg/mL of SIRO analog from pretreatment reagent is equivalent to 46.7 µg/mL of SIRO analog added from sample (Calculation: 70 µL×10 µg/mL/15 µL=46.7 µg/mL)
4) Measured sirolimus value at 0 ng/mL calibrator.
5) Measure value/46.7 is % cross-reactivity.

TABLE 1

| Instrument signal observed for calibrators | | | | | |
|---|---|---|---|---|---|
| Drug concentration in calibrators (ng/mL) | Mixture V + VI (mAU) | Mixture IX + X (mAU) | XI (mAU) | FKE (mAU) | Tacro (mAU) |
| 0.0 | 223 | 441 | 443 | 200 | 199 |
| 5.1 | 281 | 450 | 447 | 273 | 242 |
| 10.1 | 317 | 452 | 451 | 320 | 261 |
| 20.6 | 359 | 455 | 450 | 375 | 300 |
| 31.6 | 395 | 454 | 448 | 404 | 339 |
| Drug concentration measured in ng/mL | | | | | |
| Drug concentration in calibrators (ng/mL) | Mixture V + VI (ng/mL) | Mixture IX + X (ng/mL) | XI (ng/mL) | FKE (ng/mL) | Tacro (ng/mL) |
| 0.0 | 1.4 | 69.2 | 72.7 | 0.0 | −0.1 |
| 5.1 | 5.8 | 93.8 | 82.5 | 5.1 | 2.6 |
| 10.1 | 9.7 | 100.7 | 96.4 | 10.1 | 4.1 |
| 20.6 | 16.8 | 119.9 | 94.0 | 20.5 | 7.7 |
| 31.6 | 27.5 | 113.0 | 85.2 | 31.6 | 13.0 |
| Percent (%) displaced vs. SIRO | | | | | |
| Drug concentration in calibrators (ng/mL) | Mixture V + VI (%) | Mixture IX + X (%) | XI (%) | FKE (%) | Tacro (%) |
| 0.0 | | | | | |
| 5.1 | 114 | 1844 | 1622 | 100 | 52 |
| 10.1 | 96 | 994 | 951 | 100 | 40 |

TABLE 1-continued

| | | | | | |
|---|---|---|---|---|---|
| 20.6 | 82 | 584 | 458 | 100 | 38 |
| 31.6 | 87 | 357 | 269 | 100 | 41 |

Calculated antibody cross-reactivity (percent (%) times 100) measured at drug concentration in calibrator of 0 ng/mL concentration

| Drug concentration in calibrators (ng/mL) | Mixture V + VI (% × 100) | Mixture IX + X (% × 100) | XI (% × 100) | FKE (% × 100) | Tacro (% × 100) |
|---|---|---|---|---|---|
| 0 | 0.29 | 14.82 | 15.56 | 0.00 | 0.00 |

The above format for releasing an analyte (using the concentration of releasing agent (Displacer) shown) and conducting an assay for the analyte was repeated for samples containing tacrolimus. The results are summarized in Table 2.

TABLE 2

Instrument signal observed for calibrators

| Drug concentration in calibrators (ng/mL) | Mixture V + VI (mAU) | Mixture IX + X (mAU) | XI (mAU) | SIRO (mAU) |
|---|---|---|---|---|
| 0.0 | 26 | 21 | 23 | 20 |
| 2.6 | 42 | 39 | 36 | 41 |
| 5.3 | 51 | 49 | 42 | 53 |
| 11.6 | 66 | 66 | 55 | 71 |
| 30.1 | 89 | 88 | 79 | 96 |

Drug concentration measured in ng/mL

| Drug concentration in calibrators (ng/mL) | Mixture V + VI (ng/mL) | Mixture IX + X (ng/mL) | XI (ng/mL) | SIRO (ng/mL) |
|---|---|---|---|---|
| 0.0 | 0.6 | 0.0 | 0.3 | 0.0 |
| 2.6 | 2.9 | 2.4 | 1.8 | 2.6 |
| 5.3 | 4.7 | 4.1 | 2.9 | 5.3 |
| 11.6 | 9.5 | 9.2 | 5.6 | 11.6 |
| 30.1 | 23.5 | 22.6 | 16.0 | 30.1 |

Percent (%) displaced vs. SIRO

| Drug concentration in calibrators (ng/mL) | Mixture V + VI (%) | Mixture IX + X (%) | XI (%) | SIRO (%) |
|---|---|---|---|---|
| 0.0 | | | | |
| 2.6 | 111 | 90 | 68 | 100 |
| 5.3 | 89 | 78 | 54 | 100 |
| 11.6 | 82 | 79 | 48 | 100 |
| 30.1 | 78 | 75 | 53 | 100 |

Calculated antibody cross-reactivity (percent (%) times 100) measured at drug concentration in calibrator of 0 ng/mL concentration

| Drug concentration in calibrators (ng/mL) | Mixture V + VI (% × 100) | Mixture IX + X (% × 100) | XI (% × 100) | SIRO (% × 100) |
|---|---|---|---|---|
| 0 | 0.13 | 0.01 | 0.06 | 0.00 |

The results demonstrate that examples of compounds (mixture of V and VI) in accordance with the principles described herein were suitable as a releasing agents for both sirolimus and tacrolimus analytes in separate assays for sirolimus and tacrolimus. Compounds not in accordance with the principles described herein (mixture of IX and X, XI, SIRO, Tacro, and FKE) but tested for purposes of comparison exhibited lower displacement efficiency than that exhibited by the compounds in accordance with the principles described herein. Both the mixture of IX and X and compound XI demonstrated higher cross-reactivity with the sirolimus assay antibody and, therefore, are not suitable to be used as releasing agents in the sirolimus immunoassay.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims. Furthermore, the foregoing description, for purposes of explanation, used specific nomenclature to provide a thorough understanding of the invention. However, it will be apparent to one skilled in the art that the specific details are not required in order to practice the invention. Thus, the foregoing descriptions of specific embodiments of the present invention are presented for purposes of illustration and description; they are not intended to be exhaustive or to limit the invention to the precise forms disclosed. Many modifications and variations are possible in view of the above teachings. The embodiments were chosen and described in order to explain the principles of the invention and its practical applications and to thereby enable others skilled in the art to utilize the invention.

What is claimed is:

1. A composition for releasing an FKBP-binding immunosuppressant drug from endogenous binding substances in a sample suspected of containing the FKBP-binding immunosuppressant drug, the composition comprising:
   (a) a compound of the formula:

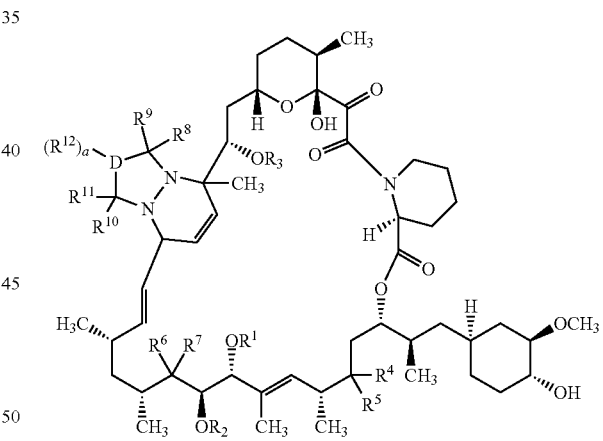

wherein:
$R^1$, $R^2$ and $R^3$ are each independently H or lower alkyl;
$R^4$ and $R^5$ are each independently H, lower hydrocarbyl or lower hydrocarbyloxy or taken together to form a double bond to O, $CH_2$, N-alkyl, or N—O-alkyl;
$R^6$ and $R^7$ are each independently H, lower hydrocarbyl or lower hydrocarbyloxy or taken together to form a double bond to O, $CH_2$, or N-alkyl, or N—O-alkyl;
$R^8$ and $R^9$ are each independently H, non-bulky organic radical or a bulky organic radical, or are taken together to form a double bond to O or $CH_2$;
$R^{10}$ and $R^{11}$ are each independently H, non-bulky organic radical or a bulky organic radical, or are taken together to form a double bond to O or $CH_2$;
$R^{12}$ is H, non-bulky hydrocarbyl or a bulky organic radical;

wherein at least one of $R^8$, $R^9$, $R^{10}$, $R^{11}$ or $R^{12}$ is a bulky organic radical;
a is 0 or 1; and
D is N, O, or CH, with the proviso that a is 0 when D is O; and
(b) a buffered medium.

2. The composition according to claim 1 wherein:
$R^1$ is H and $R^2$ and $R^3$ are each independently lower alkyl;
$R^4$ and $R^5$ are taken together to form a double bond to O;
$R^6$ and $R^7$ are taken together to form a double bond to O;
$R^8$ and $R^9$ are taken together to form a double bond to O;
$R^{10}$ and $R^{11}$ are taken together to form a double bond to O;
$R^{12}$ is aryl;
a is 1;
D is N.

3. The composition according to claim 1 wherein the compound has the formula:

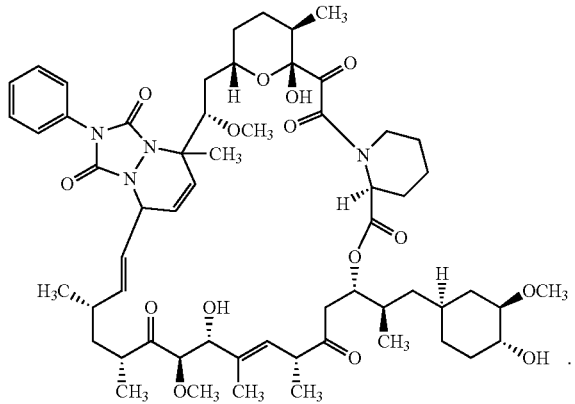

4. A method of releasing an FKBP-binding immunosuppressant drug from endogenous binding substances in a sample suspected of containing the FKBP-binding immunosuppressant drug, the method comprising:
providing in combination the sample and a composition according to claim 1 in an amount sufficient to release the FKBP-binding immunosuppressant drug from endogenous binding substances and
incubating the combination under conditions sufficient to release the FKBP-binding immunosuppressant drug from endogenous binding substances.

5. A method of releasing an FKBP-binding immunosuppressant drug from endogenous binding substances in a sample suspected of containing the FKBP-binding immunosuppressant drug, the method comprising:
providing in combination the sample and a composition according to claim 2 in an amount sufficient to release the FKBP-binding immunosuppressant drug from endogenous binding substances and
incubating the combination under conditions sufficient to release the FKBP-binding immunosuppressant drug from endogenous binding substances.

6. The composition according to claim 1 further comprising a hemolytic agent.

7. The composition according to claim 6 wherein the hemolytic agent is selected from the group consisting of detergents, low ionic strength aqueous solutions, bacterial agents, and antibodies that cause complement dependent lysis.

8. The composition according to claim 1 further comprising one or more of an anti-blood clotting agent and a preservative.

9. A method of releasing an FKBP-binding immunosuppressant drug from endogenous binding substances in a sample suspected of containing the FKBP-binding immunosuppressant drug, the method comprising:
providing in combination the sample and, in an amount sufficient to release the FKBP-binding immunosuppressant drug from endogenous binding substances, a compound of the formula:

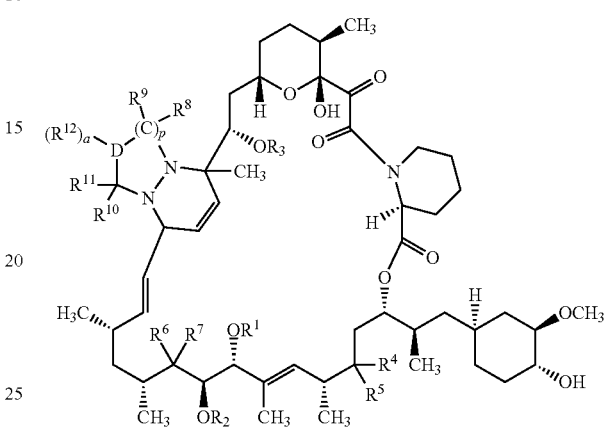

wherein:
$R^1$, $R^2$ and $R^3$ are each independently H or lower alkyl;
$R^4$ and $R^5$ are each independently H, lower hydrocarbyl or lower hydrocarbyloxy or taken together to form a double bond to O, $CH_2$, N-alkyl, or N—O-alkyl;
$R^6$ and $R^7$ are each independently H, lower hydrocarbyl or lower hydrocarbyloxy or taken together to form a double bond to O, $CH_2$, or N-alkyl, or N—O-alkyl;
$R^8$ and $R^9$ are each independently H, non-bulky organic radical or a bulky organic radical, or are taken together to form a double bond to O or $CH_2$;
$R^{10}$ and $R^{11}$ are each independently H, non-bulky organic radical or a bulky organic radical, or
are taken together to form a double bond to O or $CH_2$;
$R^{12}$ is H, non-bulky hydrocarbyl or a bulky organic radical;
wherein at least one of $R^8$, $R^9$, $R^{10}$, $R^{11}$ or $R^{12}$ is a bulky organic radical;
p is 1;
a is 0 or 1; and
D is N, O, or CH, with the proviso that a is 0 when D is O; and
incubating the combination under conditions sufficient to release the FKBP-binding immunosuppressant drug from endogenous binding substances.

10. The method according to claim 9 wherein in the formula for the compound: $R^1$ is H and $R^2$ and $R^3$ are each independently lower alkyl;
$R^4$ and $R^5$ are taken together to form a double bond to O;
$R^6$ and $R^7$ are taken together to form a double bond to O;
$R^8$ and $R^9$ are taken together to form a double bond to O;
$R^{10}$ and $R^{11}$ are taken together to form a double bond to O;
$R^{12}$ is aryl;
a is 1;
D is N.

11. A method of determining one or both of the presence and amount of an FKBP-binding immunosuppressant drug in a sample suspected of containing the FKBP-binding immunosuppressant drug, the method comprising:

(a) providing in combination in a medium:
  (i) the sample, and
  (ii) a releasing agent for releasing the FKBP-binding immunosuppressant drug from endogenous binding substances, wherein the releasing agent is a compound of the formula:

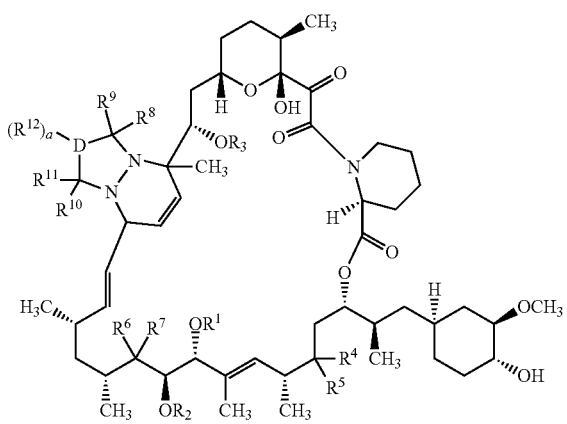

wherein:
$R^1$, $R^2$ and $R^3$ are each independently H or lower alkyl;
$R^4$ and $R^5$ are each independently H, lower hydrocarbyl or lower hydrocarbyloxy or taken together to form a double bond to O, $CH_2$, N-alkyl, or N—O-alkyl;
$R^6$ and $R^7$ are each independently H, lower hydrocarbyl or lower hydrocarbyloxy or taken together to form a double bond to O, $CH_2$, N-alkyl, or N—O-alkyl;
$R^8$ and $R^9$ are each independently H, non-bulky organic radical or a bulky organic radical, or are taken together to form a double bond to O or $CH_2$;
$R^{10}$ and $R^{11}$ are each independently H, non-bulky organic radical or a bulky organic radical, or are taken together to form a double bond to O or $CH_2$;
$R^{12}$ is H, non-bulky hydrocarbyl or a bulky organic radical;
wherein at least one of $R^8$, $R^9$, $R^{10}$, $R^{11}$ or $R^{12}$ is a bulky organic radical;
p is 1;
a is 0 or 1; and
D is N, O, or CH, with the proviso that a is 0 when D is O;
  (b) incubating the medium under conditions for releasing the FKBP-binding immunosuppressant drug from endogenous binding substances,
  (c) adding to the medium reagents for determining the presence and/or amount of the FKBP-binding immunosuppressant drug in the sample wherein the reagents comprise at least one specific binding member for the FKBP-binding immunosuppressant drug, and
  (d) examining the medium for the presence of a complex comprising the FKBP-binding immunosuppressant drug and the specific binding member for the FKBP-binding immunosuppressant drug, the presence and/or amount of the complex indicating the presence and/or amount of the FKBP-binding immunosuppressant drug in the sample.

12. The method according to claim 11 wherein in the compound of the releasing agent:
$R^1$ is H and $R^2$ and $R^3$ are each independently lower alkyl;
$R^4$ and $R^5$ are taken together to form a double bond to O;
$R^6$ and $R^7$ are taken together to form a double bond to O;
$R^8$ and $R^9$ are taken together to form a double bond to O;
$R^{10}$ and $R^{11}$ are taken together to form a double bond to O;
$R^{12}$ is aryl;
a is 1;
D is N.

13. The method according to claim 11 wherein the compound of the releasing agent has the formula:

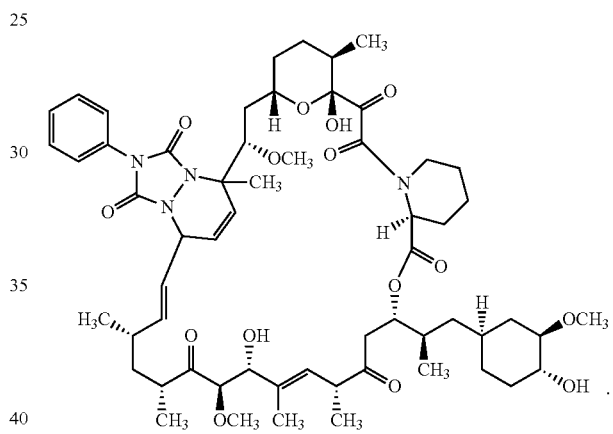

14. The method according to claim 11 wherein the reagents in step (c) further comprises an analog of the FKBP-binding immunosuppressant drug that comprises a label.

15. The method according to claim 11 wherein in step (c) a second specific binding member is added to the medium wherein the second specific binding member binds to the complex.

* * * * *